United States Patent
Tang et al.

(10) Patent No.: US 10,072,306 B2
(45) Date of Patent: Sep. 11, 2018

(54) COMPOSITIONS AND METHODS FOR THE DETECTION AND ANALYSIS OF MYCOBACTERIUM TUBERCULOSIS

(71) Applicant: ABBOTT MOLECULAR INC., Des Plaines, IL (US)

(72) Inventors: Ning Tang, Des Plaines, IL (US); Gregor Leckie, Des Plaines, IL (US); Vihanga Pahalawatta, Des Plaines, IL (US); Andrea Frank, Des Plaines, IL (US); John Lampinen, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 118 days.

(21) Appl. No.: 14/793,241

(22) Filed: Jul. 7, 2015

(65) Prior Publication Data

US 2016/0024561 A1    Jan. 28, 2016

Related U.S. Application Data

(60) Provisional application No. 62/028,527, filed on Jul. 24, 2014.

(51) Int. Cl.
C12P 19/34    (2006.01)
C12Q 1/689    (2018.01)

(52) U.S. Cl.
CPC ................... C12Q 1/689 (2013.01)

(58) Field of Classification Search
CPC ................................... C12Q 1/689
USPC ...................................... 435/91.2
See application file for complete search history.

(56) References Cited

U.S. PATENT DOCUMENTS

| | | |
|---|---|---|
| 4,948,882 A | 8/1990 | Ruth |
| 5,034,506 A | 7/1991 | Summerton et al. |
| 5,142,047 A | 8/1992 | Summerton et al. |
| 5,185,444 A | 2/1993 | Summerton et al. |
| 5,210,015 A | 5/1993 | Gelfand et al. |
| 5,370,998 A * | 12/1994 | Crawford ............... C12Q 1/689 435/6.12 |
| 5,424,414 A | 6/1995 | Mattingly |
| 5,464,746 A | 11/1995 | Fino |
| 5,627,030 A | 5/1997 | Pandian et al. |
| 5,786,149 A | 7/1998 | Leckie et al. |
| 5,925,517 A | 7/1999 | Tyagi et al. |
| 6,103,476 A | 8/2000 | Tyagi et al. |
| 6,150,097 A | 11/2000 | Tyagi et al. |
| 8,143,386 B2 | 3/2012 | Reed et al. |
| 2009/0137406 A1 | 5/2009 | Kinoshita et al. |
| 2013/0210005 A1 | 8/2013 | Kim |
| 2013/0323224 A1 | 12/2013 | Ojha et al. |

FOREIGN PATENT DOCUMENTS

| | | |
|---|---|---|
| EP | 2035440 | 3/2009 |
| WO | WO-9220702 A1 | 11/1992 |
| WO | WO-1995031570 | 11/1995 |
| WO | WO-2005012560 | 2/2005 |
| WO | WO 2008127921 | 10/2008 |
| WO | WO 2008140478 | * 11/2008 |
| WO | WO-2008152636 | 12/2008 |
| WO | WO-2010132054 | 11/2010 |

OTHER PUBLICATIONS

Ashkin et al., Indian Journal of Medical Microbiology, vol. 31, No. 4, Oct.-Dec. 2013, pp. 370-373.*
Andersen A.B., et al., "Structure and Mapping of Antigenic Domains of Protein Antigen B, A 38,000-molecular-weight Protein of Mycobacterium Tuberculosis," Infection and Immunity, 1989, vol. 57 (8), pp. 2481-2488.
Banada P.P., et al., "Containment of Bioaerosol Infection Risk by the Xpert Mtb/rif Assay and its Applicability to Point-of-care Settings," Journal of Clinical Microbiology, 2010, vol. 48 (10), pp. 3551-3557.
Gilpin C.M., et al., "Failure of Commercial Ligase Chain Reaction to Detect Mycobacterium Tuberculosis Dna in Sputum Samples from a Patient with Smear-positive Pulmonary Tuberculosis Due to a Deletion of the Target Region," Journal of Clinical Microbiology, 2002, vol. 40 (6), pp. 2305-2307.
Martin.P., et al, "Ein Neuer Zugang Zu 2'-O-Alkylribonucleosiden Und Eigenschaften Deren Oligonculeotide," Helvetica Chimica Acta , 1995, vol. 78, pp. 486-504.
Mathema B., et al., "Molecular Epidemiology of Tuberculosis: Current Insights," Clinical Microbiology Reviews, 2006, vol. 19 (4), pp. 658-685.
Nielsen P.E., et al., "Sequence-selective Recognition of DNA by Strand Displacement with a Thymine-substituted Polyamide," Science, 1991, vol. 254 (5037), pp. 1497-1500.
Thierry D., et al., "Is6110, an Is-like Element of Mycobacterium Tuberculosis Complex," Nucleic Acids Research, 1990, vol. 18 (1), pp. 188.
Tortoli E.P., et al., "Use of Bactec Mgit 960 for Recovery of Mycobacteria from Clinical Specimens: Multicenter Study," Journal of Clinical Microbiology, 1999, vol. 37 (11), pp. 3578-3582.
Wallis R.S., et al., "Drug Tolerance in Mycobacterium Tuberculosis," Antimicrobial Agents and Chemotherapy, 1999, vol. 43 (11), pp. 2600-2606.
Warren R.M., et al., "Differentiation of Mycobacterium Tuberculosis Complex by Pcr Amplification of Genomic Regions of Difference," The International Journal of Tuberculosis and lung Disease, 2006, vol. 10 (7), pp. 818-822.
International Search Report and Written Opinion for Application No. PCT/US2015/039362, dated Nov. 30, 2015, 18 pages.

(Continued)

*Primary Examiner* — Cynthia B Wilder
(74) *Attorney, Agent, or Firm* — Casimir Jones, S.C.; David Casimir

(57) ABSTRACT

Provided herein are compositions and methods useful for the detection of MTB. In particular, provided herein are kits, reagents, reaction mixtures, and methods involving such for nucleic acid amplification and detection procedures, which specifically and sensitively detect MTB in samples.

13 Claims, 3 Drawing Sheets
Specification includes a Sequence Listing.

(56) References Cited

OTHER PUBLICATIONS

Kusum et al., "Multiplex PCR for rapid diagnosis of tuberculous meningitis." J Neurol. Oct. 2011;258(10):1781-7.
Leung et al., "Rapid and simultaneous detection of *Mycobacterium tuberculosis* complex and Beijing/W genotype in sputum by an optimized DNA extraction protocol and a novel multiplex real-time PCR." J Clin Microbiol. Jul. 2011;49(7):2509-15. Retrieved from the Internet:URL:http:fjjcm.asm.orgjcontent/49/7/2509, Abstract Only.
Savelkoul et al., "Detection of *Mycobacterium tuberculosis* complex with Real Time PCR: comparison of different primer-probe sets based on the IS6110 element." J Microbiol Methods. Jul. 2006;66(1):177-80.
Sharma et al., "Evaluation of multiplex polymerase chain reaction utilising multiple targets in *Mycobacterium tuberculosis* direct test negative but culture positive cases: a potential method for enhancing the diagnosis of tuberculosis." Indian J Med Microbiol. Oct.-Dec. 2013;31(4):370-3.
Search Report of related EP 15824241.2, dated Nov. 20, 2017, 10 pages.

\* cited by examiner

ASSAY WORK FLOW:

COMPOSITIONS AND METHODS FOR THE DETECTION AND ANALYSIS OF MYCOBACTERIUM TUBERCULOSIS

FIELD OF THE INVENTION

The present invention relates to *mycobacterium tuberculosis*. In particular, the invention relates to compositions and method for detecting *mycobacterium tuberculosis*.

BACKGROUND OF THE INVENTION

*Mycobacterium tuberculosis* (MTB) constitutes a serious threat to public health in the world and is second only to HIV/AIDS as the greatest killer worldwide due to a single infectious agent (Warren et al, Differentiation of *Mycobacterium tuberculosis* complex by PCR amplification of genomic regions of difference, 2006 July, Int J Tuberc Lung Dis. 10 (7):818-822). The CDC reports that in 2011, there were an estimated 8.7 million new cases of MTB (13% co-infected with HIV); 1.4 million people died from MTB, including almost one million deaths among HIV-negative individuals and 430,000 among people who were HIV-positive. The World Health Organization (WHO) reports that MTB is one of the top killers of women, with 300,000 deaths among HIV-negative women and 200,000 deaths among HIV-positive women in 2011. It is among the top three causes of death for women aged 15 to 44. MTB is also a leading killer of people living with HIV causing one quarter of all deaths. There were an estimated 0.5 million cases and 64,000 deaths among children in 2011. Multi-drug resistant MTB (MDR-TB) is increasing and is present in virtually all countries surveyed. Geographically, the burden of MTB is highest in Asia and Africa. WHO reported that overall MTB case detection is still less than 60% in low-income countries (LICs) and only 66% globally. That is, of an estimated 8.7 million people who become ill with MTB in 2011, 2.9 million with active disease were not diagnosed and notified to national MTB control programs. In addition, only 19% of MDR-MTB cases were appropriately diagnosed and notified. Fewer than 1 in 20 new MTB patients have access to drug susceptibility testing. Due to the risk of spread of MTB, the potential for the emergence of drug-resistant strains, and the severity of the disease in patients infected with HIV-1, a low price, prompt and accurate MTB molecular test is extremely important. Routine cultures are time-consuming and can take up to six weeks. Microscopic examination of acid-fast smears is the most rapid method for the detection of mycobacteria, but it is insensitive and non-specific.

SUMMARY OF THE INVENTION

Provided herein are compositions and methods useful for the detection of MTB. In particular, provided herein are kits, reagents, reaction mixtures, and methods involving such for nucleic acid amplification and detection procedures, which specifically and sensitively detect MTB in samples. Such compositions and method include primers, probes, primer sets, primer and probe sets, and methods for detecting MTB complex in different human samples such as sputum, bronchial alveolar lavage (BAL) and N-acetyl-L-cysteine (NALC)-NaOH sediments of sputum and BAL samples.

In some embodiments, two or more of the polynucleotide reagents provided herein as SEQ ID NOS: 1-9 are combined in a composition (e.g., reagent set, kit, reaction mixture, etc.). In some embodiments, one or more or all of the nucleic acid reagents comprise a detectable moiety (e.g., synthetic label). In some embodiments, the compositions comprise one or more primers SEQ ID NOS: 1-4 or 7-8. In some embodiments, the compositions comprise one or more primer pairs SEQ ID NOS: 1 and 2, 3 and 4, or 7 and 8. In some embodiments, the compositions comprise one or more probes (e.g., labeled probes) of SEQ ID NOS: 5, 6, or 9. In some embodiments, the compositions comprise primer and probe sets: SEQ ID NOS 1-2 and 5, 3-4 and 6, or 7-9. In some embodiments, the compositions comprise internal control reagents, such as SEQ ID NOS: 7-9. In some embodiments, the compositions comprise a dual probe system comprising SEQ ID NOS: 5 and 6.

In some embodiments, the compositions and methods employ reagents sets comprising a polynucleotide component having primers, probes, primers sets, and/or probe sets. In some embodiments, the polynucleotide component of the composition consists of the primer, probe, primer set, or probe set combinations described above. As reaction mixtures, the compositions may consist of such polynucleotides as well as any polynucleotides included in a sample (i.e., the only non-sample nucleic acid molecules are the polynucleotides represented by SEQ ID NOs: 1-9, individually or in combinations (e.g., the combinations described above).

The primer sets herein provided comprise two primers, and are useful for the amplification of target sequences, e.g., in PCR. In some embodiments, the compositions comprise at least two primers and one or more (e.g., two or more) probes that detect amplicons generated by the primers.

Also provided herein are methods for detecting MTB in a sample. In some embodiments, the methods comprise (a) forming a reaction mixture comprising nucleic acid amplification reagents, at least polynucleotide primer or probe described herein, and a test sample potentially containing at least one target sequence; and (b) subjecting the mixture to amplification conditions to generate at least one copy of a nucleic acid sequence complementary to the target sequence. In some embodiments the method further comprises detecting generated amplicons. In some embodiments, the detecting comprises (c) hybridizing a probe to the nucleic acid sequence complementary to the target sequence so as to form a hybrid comprising the probe and the nucleic acid sequence complementary to the target sequence; and (d) detecting, directly or indirectly, the hybrid as an indication of the presence of MTB in the test sample.

Further, when the amplification is PCR, or a similar thermocycling amplification process, step (b) can be repeated multiple times to increase the number of target sequence copies.

According to another embodiment, both MTB and one or more additional infectious agents (e.g., HIV) or other nucleic acid molecules (e.g., human sequences) are detected. Accordingly, in some embodiments, compositions comprise reagents for detecting such other agents or nucleic acid molecules.

In some embodiments, the compositions and methods further employ control reagents or kit components (e.g., positive controls, negative controls). In some embodiments, the control reagents include a synthetic target nucleic acid. In some embodiments, the control reagents include reagents for detecting an MTB, human, or other sequence expected to be present in a sample. In some embodiments, a control target nucleic acid, whether synthetic or endogenous in a sample, is selected such that amplification primers that amplify the MTB target nucleic acid also amplify the control target nucleic acid. In some such embodiments, a probe that detects the MTB target nucleic acid or an amplicon generated therefrom does not detect the control target or an amplicon generated therefrom. In some embodiments, a control probe is provided that detects the control target nucleic acid or an amplicon generated therefrom but does not detect the MTB target nucleic acid or an amplicon generated therefrom. In some embodiments, internal standards are provided for quantitation.

In some embodiments, kits, in addition to the reagents discussed above, include one or more suitable containers, instructions for use, software (e.g., data analysis software), and the like. In some embodiments, kits include reagents for labeling polynucleotides. In some embodiments, one or more components in the kit is in lyophilized form.

Embodiments of the present disclosure provide compositions, kits, systems, and methods for identifying MTB in complex biological samples such as sputum or bronchoalveolar lavage and sediments thereof. In some embodiments, the compositions and methods provide inactivation reagents, and single probe or multiple probe real time detection methods that are able to specifically and accurately isolate and identify MTB.

For example, in some embodiments, the present disclosure provides a composition, comprising: at least one (e.g., one, two, or three) primer pair(s) selected from SEQ ID NOS: 1 and 2, SEQ ID NOS: 3 and 4, or SEQ ID NOS: 7 and 8. In some embodiments, the composition comprises SEQ ID NOS: 1-4 and 7-8. In some embodiments, the composition further comprises at least one probe selected from SEQ ID NOS: 5, 6, or 9.

Further embodiments provide a composition, comprising: a set of primer pairs of SEQ ID NOS: 1 and 2 and SEQ ID NOS: 3 and 4. In some embodiments, the composition further comprises at least one probe selected from SEQ ID NOS: 5, 6, or 9. In some embodiments, the composition further comprises the primer pair of SEQ ID NOS: 7 and 8.

Additional embodiments provide a composition, comprising each the nucleic acids of SEQ ID NOS: 1-9. In some embodiments, the above compositions include or are substituted with one or more nucleic acid sequences selected from the SEQ ID NOS: 10-36.

Embodiments of the disclosure provide a kit, comprising: a) any of the aforementioned compositions, and b) at least one reagent for performing a nucleic acid amplification reaction (e.g., a nucleic acid polymerase; a plurality of dNTPS, a buffer, or an inactivation reagent). In some embodiments, the inactivation reagent comprises water, a detergent, an alcohol, and NaOH (e.g., isopropanol, sodium hydroxide, TWEEN-20, and water).

In other embodiments, the disclosure provides a reaction mixture, comprising: any of the aforementioned compositions or nucleic acids hybridized to a microbacterium tuberculosis (MTB) nucleic acid. In some embodiments, the MTB target nucleic acid is one or more (e.g., both) of insertion sequence (IS) 6110 and Protein Antigen B (PAB).

In further embodiments, the present disclosure provides a method of identifying an MTB nucleic acid in a biological sample, comprising: a) contacting a biological sample from a subject with any of the aforementioned nucleic acid primers or probes, and b) directly or indirectly detecting the binding of the nucleic acid primers or probes to the MTB nucleic acid. In some embodiments, the method further comprises the step of c) determining the presence of MTB in the sample when the binding is detected. In some embodiments, the detecting is via real time PCR detecting. In some embodiments, the method further comprises the step of inactivating MTB in the sample using the inactivation buffer. In some embodiments, the sample is sputum, bronchoalveolar lavage [BAL], or N-acetyl-L-cysteine [NALC] sediments of sputum and BAL. In some embodiments, the method further comprises the step of extracting DNA from the sample following inactivation.

Yet other embodiments provide a method of detecting an MTB nucleic acid in a biological sample, comprising: a) inactivating the biological sample with an inactivating reagent to generate an inactivated sample; b) extracting DNA from the inactivated sample; c) contacting the DNA with one or more primer pairs and one or more nucleic acid probes; d) performing an amplification assay to amplify one or more MTB nucleic acid targets; and e) identifying the presence of the targets in the sample.

Further embodiments provide a method of detecting an MTB nucleic acid in a biological sample, comprising: a) inactivating said biological sample with an inactivating reagent comprising isopropanol, sodium hydroxide, TWEEN-20, and water to generate an inactivated sample; b) extracting DNA from the inactivated sample; c) contacting the DNA with one or more primer pairs selected from SEQ ID NOS: 1 and 2 and SEQ ID NOS: 3 and 4; and one or more nucleic acid probes selected from SEQ ID NOS: 5 and 6; d) performing an amplification assay to amplify one or more MTB nucleic acid targets; and e) identifying the presence of the targets in said sample.

Additional embodiments provide a method of detecting an MTB nucleic acid in a biological sample, comprising: a) inactivating said biological sample with an inactivating reagent to generate an inactivated sample; b) extracting DNA from the inactivated sample; c) contacting the DNA with one or more primer pairs selected from SEQ ID NOS: 1 and 2 and SEQ ID NOS: 3 and 4; and one or more nucleic acid probes selected from SEQ ID NOS: 5 and 6; d) performing an amplification assay to amplify one or more MTB nucleic acid targets; and e) identifying the presence of the targets in the sample.

Other embodiments provide a method of detecting an MTB nucleic acid in a biological sample, comprising: a) inactivating the biological sample with an inactivating reagent to generate an inactivated sample; b) extracting DNA from the inactivated sample; c) contacting the DNA with one or more primer pairs selected from SEQ ID NOS: 1 and 2 and SEQ ID NOS: 3 and 4; and one or more nucleic acid probes selected from SEQ ID NOs: 5 and 6; d) performing a real time PCR assay to amplify one or more MTB nucleic acid targets; and e) identifying the presence of the targets in the sample.

Still other embodiments provide a method of detecting an MTB nucleic acid in a biological sample, comprising: a) inactivating the biological sample with an inactivating reagent to generate an inactivated sample; b) extracting DNA from the inactivated sample; c) contacting said DNA with one or more primer pairs selected from SEQ ID NOS: 1 and 2 and SEQ ID NOS: 3 and 4; and one or more nucleic acid probes selected from SEQ ID NOS: 5 and 6; d) performing an amplification assay to amplify one or more MTB nucleic acid targets selected from IS6110 and PAB; and e) identifying the presence of the targets in the sample.

In certain embodiments, the present disclosure provides a method of detecting an MTB nucleic acid in a biological sample, comprising: a) inactivating the biological sample with an inactivating reagent to generate an inactivated sample; b) extracting DNA from the inactivated sample; c) contacting the DNA with the primer pairs of SEQ ID NOS: 1 and 2 and SEQ ID NOS: 3 and 4; and the nucleic acid probes of SEQ ID NOS: 5 and 6; d) performing an amplification assay to amplify one or more MTB nucleic acid targets; and e) identifying the presence of the targets in the sample.

In some embodiments, the present disclosure provides a method of detecting an MTB nucleic acid in a biological sample, comprising: a) inactivating the biological sample with an inactivating reagent comprising isopropanol, sodium hydroxide, TWEEN-20, and water to generate an inactivated sample; b) extracting DNA from the inactivated sample; c) contacting the DNA with the primer pairs of SEQ ID NOS: 1 and 2 and SEQ ID NOS: 3 and 4; and the nucleic acid probes of SEQ ID NOS: 5 and 6; d) performing an amplification assay to amplify one or more MTB nucleic acid targets; and e) identifying the presence of the targets in the sample.

Additional embodiments are described herein.

DETAILED DESCRIPTION

Figure 1:
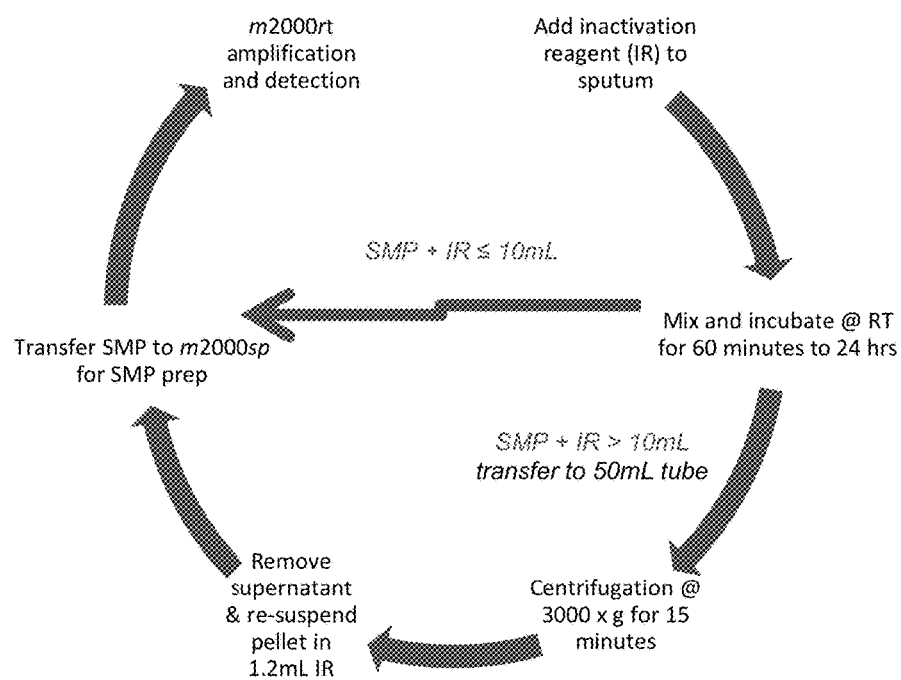
FIG. 1 shows an MTB assay work-flow diagram in some embodiments of the technology provided herein.

Provided herein are compositions and methods useful for the detection of MTB. In particular, provided herein are kits, reagents, reaction mixtures, and methods involving such for nucleic acid amplification and detection procedures, which specifically and sensitively detect MTB in samples.

In some embodiments, provided herein are polynucleotides that specifically hybridize with a nucleic acid sequence, or complement thereof, of MTB. These polynucleotides find use to amplify MTB, if present in a sample, and to specifically detect the presence of MTB. Exemplary polynucleotides are described, for example, by SEQ ID NOS: 1-9 or 10-36.

In some embodiments, assays described herein utilize multiple (e.g., two) different MTB-specific primer/probe sets. For example, in some embodiments, a first set is designed to detect the multi-copy insertion element, IS6110 (Thierry D, et al., Nucleic Acids Res 1990; 18:188), and second set, the single copy gene, PAB (Anderson A B, Hansen E B, Infect Immun 1989; 57:2481-2488). Because there have been reports of MTB strains that lack IS6110 (Mathema B, et al., Clinical Microbiology Reviews 2006; 19:658-685), or that have a deletion in the PAB gene (Gilpin C M, et al., J Clin Microbiol 2002; 40:2305-2307), the use of both targets minimizes the risk of false negative results. Experiments described herein demonstrated that the dual target strategy results in the detection of MTB genomic DNA with high reliability.

The mycobacterial cell wall is resistant to conventional cell lysis techniques due to the complex structure of lipophilic molecules and polysaccharides. Thus, in some embodiments, MTB detection assays utilize a guanidinium thiocyanate-magnetic microparticle purification method with optimized incubation temperatures and mixing conditions for TB cell lyses and genomic DNA release. Experiments conducted during the development of embodiments of the assays described herein showed that the sample DNA extraction method is comparable in efficiency to mechanical bead beating for TB cell lyses.

Further experiments demonstrated that all 66 MTB complex DNAs (including eight different MTB complex species) were detected by the assay. Reliability of the assay was assessed in four ways. First, specificity of the assay was assessed by testing 80 potentially different cross-reactors. None of the potential cross-reactors were detected. Second, a carryover assessment was performed in which high positive MTB samples were processed alongside negative samples to determine if false positives, or carryover, were detected in the negative samples. No false positives were observed. Third, various potentially interfering substances were tested for their impact on assay performance. No interference was observed, except with 8.3% and 5.0% bovine mucus, where interference was observed. This interference was removed when the mucus concentration was reduced to ≤2.5%. When clinical specimens were tested, the rate of specimens with invalid IC results was 0.3%, demonstrating that the sample preparation methods described herein removed PCR inhibitors in an effective manner. This provides evidence of the robustness of the protocol and indicates that the impact of interference caused by bovine mucus is likely not significant to the assay. Finally, a reproducibility study was performed in which multiple users used multiple m2000 instrument systems, or manual sample preparation, to test low positive (three times LOD) and negative panels. 100% reproducibility was observed. These data support the robust nature of the assay when used in analytical studies and clinical samples testing The clinical utility of the MTB detection assays was assessed by testing sputum and NALC specimens collected from patients suspected of having TB in five countries using both archived samples and prospectively collected samples. Overall assay sensitivity was 93%, while it was 99% in smear positive culture positive samples and 81% in smear negative culture positive samples. Specificity was 97%. The results of the analytical specificity test and the sputum sample testing from non-TB suspect population from within the U.S. all showed 100% specificity. The clinical specificity was determined based on comparison of assay results with culture results.

Embodiments of the technology described herein provide high throughput, automated MTB detection with high sensitivity and specificity. Compared with conventional culture assays, the technology significantly improves the rapid diagnosis of TB by allowing the direct detection of mycobacteria in clinical specimens. The assays provide superior sensitivity and specificity compared to conventional acid-fast smears microscopic examination. A gap with current MTB diagnostic assays is the lack of sensitivity in culture positive and smear negative populations (with low TB concentration in samples). Embodiments of the technology provided herein fill that gap. Assays provided herein are robust with very low inhibition rate even if difficult to work with sputum samples. This reduces the time required for repeat testing of invalid samples. In some embodiments, a multi-copy MTB target is interrogated, providing greater target sensitivity and less chance of false negative assay results caused by mutations/deletions in the target region. Embodiments further provide unique and effective MTB inactivation methods.

The term "specifically hybridize" as used herein refers to the ability of a nucleic acid to bind detectably and specifically to a second nucleic acid. Polynucleotides specifically hybridize with target nucleic acid strands under hybridization and wash conditions that minimize appreciable amounts of detectable binding to non-specific nucleic acids. Stringent conditions that can be used to achieve specific hybridization are known in the art.

A "target sequence" or "target nucleic acid sequence" as used herein means a nucleic acid sequence of MTB or other sequence to be detected (e.g., HIV), or complement thereof, that is amplified, detected, or both amplified and detected using one or more of the polynucleotides herein provided. Additionally, while the term target sequence sometimes refers to a double stranded nucleic acid sequence, those skilled in the art will recognize that the target sequence can also be single stranded. In cases where the target is double stranded, polynucleotide primer sequences preferably amplify both strands of the target sequence. A target sequence may be selected that is more or less specific for a particular organism. For example, the target sequence may be specific to an entire genus, to more than one genus, to a species or subspecies, serogroup, auxotype, serotype, strain, isolate or other subset of organisms.

The term "test sample" as used herein, means a sample taken from an organism, biological fluid, environmental sample, or other sample that is suspected of containing or potentially contains an MTB target sequence. The test sample can be taken from any biological source, such as for example, tissue, blood, saliva, sputa, N-acetyl-L-cysteine (NALC)-NaOH sediments of sputum, mucus, bronchial alveolar lavage (BAL), sweat, urine, urethral swabs, cervical swabs, urogenital or anal swabs, conjunctival swabs, ocular lens fluid, cerebral spinal fluid, milk, ascites fluid, synovial fluid, peritoneal fluid, amniotic fluid, fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma or serum from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

The term "label" as used herein means a molecule or moiety having a property or characteristic which is capable of detection and, optionally, of quantitation. A label can be directly detectable, as with, for example (and without limitation), radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, quenching moieties, light, and the like to enable detection and/or quantitation of the label. When indirectly detectable labels are used, they are typically used in combination with a "conjugate". A conjugate is typically a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, e.g., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

A polynucleotide is a nucleic acid polymer of ribonucleic acid (RNA), deoxyribonucleic acid (DNA), modified RNA or DNA, or RNA or DNA mimetics (such as, without limitation PNAs), and derivatives thereof, and homologues thereof. Thus, polynucleotides include polymers composed of naturally occurring nucleobases, sugars and covalent internucleoside (backbone) linkages as well as polymers having non-naturally-occurring portions that function similarly. Such modified or substituted nucleic acid polymers are well known in the art and for the purposes of the present invention, are referred to as "analogues." For ease of preparation and familiarity to the skilled artisan, polynucleotides are preferably modified or unmodified polymers of deoxyribonucleic acid or ribonucleic acid.

Polynucleotide analogues that are useful include polymers with modified backbones or non-natural internucleoside linkages. Modified backbones include those retaining a phosphorus atom in the backbone, such as phosphorothioates, chiral phosphorothioates, phosphorodithioates, phosphotriesters, aminoalkylphosphotriesters, methyl and other alkyl phosphonates, as well as those no longer having a phosphorus atom, such as backbones formed by short chain alkyl or cycloalkyl internucleoside linkages, mixed heteroatom and alkyl or cycloalkyl internucleoside linkages, or one or more short chain heteroatomic or heterocyclic internucleoside linkages. An example of such a non-phosphorus containing backbone is a morpholino linkage (see, for example, U.S. Pat. Nos. 5,185,444, 5,034,506, and 5,142,047 all of which are herein incorporated by reference). Modified nucleic acid polymers (analogues) may contain one or more modified sugar moieties. For example, sugar moieties may be modified by substitution at the 2' position with a 2-methoxyethoxy (2-MOE) group (see, for example, Martin et al., (1995) Helv. Chim. Acta, 78:486-504).

Embodiments also contemplate analogues that are RNA or DNA mimetics, in which both the sugar and the internucleoside linkage of the nucleotide units are replaced with novel groups. In these mimetics the base units are maintained for hybridization with the target sequence. An example of such a mimetic, which has been shown to have excellent hybridization properties, is a peptide nucleic acid (PNA) (Nielsen et al., (1991) Science, 254:1497-1500; International Patent Application WO 92/20702, herein incorporated by reference). In PNA compounds, the sugar-backbone of an oligonucleotide is replaced with an amide containing backbone, for example an aminoethylglycine backbone. The nucleobases are retained and are bound directly or indirectly to the aza-nitrogen atoms of the amide portion of the backbone.

Contemplated polynucleotides may further include derivatives wherein the nucleic acid molecule has been covalently modified by substitution, chemical, enzymatic, or other appropriate means with a moiety other than a naturally occurring nucleotide, for example with a moiety that functions as a label, as described herein.

The present invention further encompasses homologues of the polynucleotides having nucleic acid sequences set forth in SEQ ID NOS: 1-9 or 10-36. Homologues are nucleic acids having at least one alteration in the primary sequence set forth in any one of SEQ ID NOS: 1-9 or 10-36, that does not destroy the ability of the polynucleotide to specifically hybridize with a target sequence, as described above. Accordingly, a primary sequence can be altered, for example, by the insertion, addition, deletion or substitution of one or more of the nucleotides of, for example, SEQ ID NOS: 1-9 or 10-36. Thus, homologues that are fragments of a sequence disclosed in SEQ ID NOS: 1-9 or 10-36 may have a consecutive sequence of at least about 7, 10, 13, 14, 15, 16, 17, 18, 19 20, 21, 22, 23 or more nucleotides of the nucleic acid sequences of SEQ ID NOS: 1-9 or 10-36, and will retain the ability to specifically hybridize with a target sequence, as described above. Ordinarily, the homologues will have a nucleic acid sequence having at least about 50%, 60%, 70%, 80%, 85%, 90% or 95% nucleic acid sequence identity with a nucleic acid sequence set forth in SEQ ID NOS: 1-9 or 10-36. Identity with respect to such sequences is defined herein as the percentage of nucleotides in the candidate sequence that are identical with the known polynucleotides after aligning the sequences and introducing gaps, if necessary, to achieve the maximum percent identity. Terminal (5' or 3') or internal deletions, extensions or insertions into the nucleotide sequence shall not be construed as affecting identity.

In some embodiments, the polynucleotides comprise primers and probes that specifically hybridize to an MTB target sequence, for example the nucleic acid molecules having any one of the nucleic acid sequences set forth in SEQ ID NOS: 1-9 or 10-36, including analogues and/or derivatives of said nucleic acid sequences, and homologues thereof, that can specifically hybridize with an MTB target sequence. As described below, polynucleotides find use as primers and/or probes to amplify or detect MTB.

The polynucleotides can be prepared by a variety of techniques. For example, the polynucleotides can be prepared using solid-phase synthesis using commercially available equipment, such as that available from Applied Biosystems USA Inc. (Foster City, Calif.), DuPont, (Wilmington, Del.), or Milligen (Bedford, Mass.). Modified polynucleotides, such as phosphorothioates and alkylated derivatives, can also be readily prepared (see, for example, U.S. Pat. Nos. 5,464,746; 5,424,414; and 4,948,882).

The polynucleotides can be employed directly as probes for the detection, or quantitation, or both, of MTB nucleic acids in a test sample. The test sample is contacted with at least one of the polynucleotides under suitable hybridization conditions and the hybridization between the target sequence and at least one of the polynucleotides is then detected. Detection can be direct or indirect. In some embodiments, a hybrid between the probe and target is detected directly. In some embodiments, the hybrid is directed indirectly, for example, by detecting reaction byproducts generated by an enzymatic reaction that occurs in the presence of a duplex between a probe and the MTB target.

The polynucleotides may incorporate one or more detectable labels. Detectable labels are molecules or moieties having a property or characteristic that can be detected directly or indirectly and are chosen such that the ability of the polynucleotide to hybridize with its target sequence is not adversely affected.

Detection labels have the same definition as "labels" previously defined and "capture labels" are typically used to separate extension products, and probes associated with any such products, from other amplification reactants. Specific binding members (as previously defined) are well suited for this purpose. Also, probes used according to this method may be blocked at their 3' ends so that they are not extended under hybridization conditions. Methods for preventing extension of a probe are well known and are a matter of choice for one skilled in the art.

In cases where labels are employed to detect primer-amplified products, primer sequences optionally can be labeled with either a capture label or a detection label. In some embodiments, primer comprise a 3' portion that hybridizing to an MTB target nucleic acid and a 5' portion that introduces a non-MTB sequence to extension products generated therefrom. Such 5' portions may include a synthetic tag sequence for use, for example, in next-generation sequencing technologies.

In some embodiments, a probe is used to hybridize with the extension product or amplicon generated by the primer sequences, and typically hybridizes with a sequence that does not include the primer sequences. Similarly to the primer sequence, the probe sequence can also labeled with either a capture label or a detection label with the caveat that, in some embodiments, when the primer is labeled with a capture label, the probe is labeled with a detection label, and vice versa. Upon formation of the copy sequence/probe hybrids, the differential labels (i.e., capture and detection labels) on the copy sequence and probe sequence can be used to separate and detect such hybrids.

The polynucleotides are also suitable for use as capture probes in sandwich-type assays. Briefly, the polynucleotide capture probe is attached to a solid support and brought into contact with a test sample under suitable hybridization conditions such that a probe:target hybrid is formed between the capture probe and any target nucleic acid present in the test sample. After one or more appropriate washing steps, the probe:target hybrid is detected, usually by means of a second "disclosure" probe or by a specific antibody that recognizes the hybrid molecule.

Embodiments also contemplate the use of the polynucleotides in modified nucleic acid hybridization assays. For example, U.S. Pat. No. 5,627,030 discloses a method to amplify the detection signal in a nucleic acid hybridization assay. In the disclosed assay, a first polynucleotide probe sequence is hybridized under suitable conditions to a target sequence, the probe:target hybrid is subsequently immunocaptured and immobilized. A second polynucleotide probe which contains many repeating sequence units is then hybridized to the probe component of the probe:target hybrid. Detection is achieved by hybridization of many labeled nucleic acid sequence probes, one to each of the repeating sequence units present in the second probe. The attachment of multiple labeled probes to the second probe thus amplifies the detection signal and increases the sensitivity of the assay.

Amplification and Detection of MTB Nucleotide Sequences

The polynucleotides can be used as primers or probes to amplify and/or detect MTB in a test sample. The primer/probe sets provided herein comprise at least two primers and at least one probe. These primer/probe sets can be employed according to nucleic acid amplification techniques. Hence, the primers in any particular primer/probe set can be employed to amplify a target sequence. In most cases, the probe hybridizes to the copies of the target sequence generated by one or more of the primers and generally facilitates detecting any copies of the target sequence generated during the course of the amplification reaction. All of the primer/probe sets can be employed according to nucleic acid amplification procedures to specifically and sensitively detect MTB when the appropriate primers and probes are combined. It is contemplated that the individual primers and probes of the primer/probe sets provided herein may alternatively be used in combination with primers and/or probes other than those described in the primer/probe sets provided herein. In some embodiments, two primer and probes sets are employed to detect two different MTB target sequences.

Amplification procedures include, but are not limited to, polymerase chain reaction (PCR), TMA, rolling circle amplification, nucleic acid sequence based amplification (NASBA), and strand displacement amplification (SDA). One skilled in the art will understand that for use in certain amplification techniques the primers may need to be modified, for example, for SDA the primer comprises additional nucleotides near its 5' end that constitute a recognition site for a restriction endonuclease. Similarly, for NASBA the primer comprises additional nucleotides near the 5' end that constitute an RNA polymerase promoter.

In some embodiments, certain criteria are taken into consideration when selecting a primer for an amplification reaction. For example, when a primer pair is required for the amplification reaction, the primers should be selected such that the likelihood of forming 3' duplexes is minimized, and such that the melting temperatures ($T_M$) are sufficiently similar to optimize annealing to the target sequence and minimize the amount of non-specific annealing.

In some embodiments, the amplification methods comprises (a) forming a reaction mixture comprising nucleic acid amplification reagents, at least one primer/probe set, and a test sample suspected of containing at least one target sequence and (b) subjecting the mixture to amplification conditions to generate at least one copy of a nucleic acid sequence complementary to the target sequence. Step (b) of the above methods can be repeated any suitable number of times (prior to step (c) in the detection method), e.g., by thermal cycling the reaction mixture between 10 and 100 times, typically between about 20 and about 60 times, more typically between about 25 and about 45 times.

Nucleic acid amplification reagents include but are not limited to, an enzyme having at least polymerase activity, enzyme cofactors such as magnesium or manganese; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

Amplification conditions are conditions that generally promote annealing and extension of one or more nucleic acid sequences.

Specific amplicons produced by amplification of target nucleic acid sequences using the polynucleotides, as described above, can be detected by a variety of methods. For example, one or more of the primers used in the amplification reactions may be labeled such that an amplicon can be directly detected by conventional techniques subsequent to the amplification reaction. Alternatively, a probe consisting of a labeled version of one of the primers used in the amplification reaction, or a third polynucleotide distinct from the primer sequences that has been labeled and is complementary to a region of the amplified sequence, can be added after the amplification reaction is complete. The mixture is then submitted to appropriate hybridization and wash conditions and the label is detected by conventional methods.

The amplification product produced as above can be detected during or subsequently to the amplification of the target sequence. Methods for detecting the amplification of a target sequence during amplification (e.g., real-time PCR) are outlined above, and described, for example, in U.S. Pat. No. 5,210,015. Alternatively, amplification products are hybridized to probes, then separated from other reaction components and detected using microparticles and labeled probes.

It will be readily appreciated that a procedure that allows both amplification and detection of target nucleic acid sequences to take place concurrently in a single unopened reaction vessel would be advantageous. Such a procedure avoids the risk of "carry-over" contamination in the post-amplification processing steps, and also facilitates high-throughput screening or assays and the adaptation of the procedure to automation. Furthermore, this type of procedure allows "real-time" monitoring of the amplification reaction as well as "end-point" monitoring. Examples of probe molecules that are particularly well-suited to this type of procedure include molecular beacon probes and TAQ-MAN probes. TAQMAN probes are generally dual-labeled fluorogenic nucleic acid probes composed of a polynucleotide complementary to the target sequence that is labeled at the 5' terminus with a fluorophore and at the 3' terminus with a quencher. In the free probe, the close proximity of the fluorophore and the quencher ensures that the fluorophore is internally quenched. During the extension phase of the amplification reaction, the probe is cleaved by the 5' nuclease activity of the polymerase and the fluorophore is released. The released fluorophore can then fluoresce and thus produces a detectable signal.

In some embodiments, "molecular beacon" probes are employed. Molecular beacon probes are described, for example, in U.S. Pat. Nos. 6,150,097; 5,925,517 and 6,103,476 (herein incorporated by reference in their entireties). Basically, molecular beacons are polynucleotide probes capable of forming a stem-loop (hairpin) structure. The loop is a single-stranded structure containing sequences complementary to the target sequence, whereas the stem typically is unrelated to the target sequence and self-hybridizes to form a double-stranded region. Nucleotides that are both complementary to the target sequence and that can self-hybridize may also form part of the stem region. Attached to one arm of the stem is a fluorophore moiety and to the other arm a quencher moiety. When the polynucleotide adopts a hairpin shape, the fluorophore and the quencher are in close proximity and the energy emitted by the fluorophore is thus absorbed by the quencher and given off as heat, resulting in internal quenching of the fluorophore. Upon binding of the polynucleotide to its target sequence, the fluorophore and the quencher become spatially separated and the fluorophore can fluoresce producing a detectable signal.

Examples of fluorophores that find use include, but are not limited to, fluorescein and fluorescein derivatives such as a dihalo-($C_1$ to $C_8$)dialkoxycarboxyfluorescein, 5-(2'-aminoethyl)aminonaphthalene-1-sulphonic acid (EDANS), coumarin and coumarin derivatives, Lucifer yellow, Texas red, tetramethylrhodamine, tetrachloro-6-carboxyfluoroscein, 5-carboxyrhodamine, cyanine dyes and the like. Quenchers include, but are not limited to, DABCYL, 4'-(4-dimethylaminophenylazo)benzoic acid (DABSYL), 4-dimethylaminophenylazophenyl-4'-maleimide (DABMI), tetramethylrhodamine, carboxytetramethylrhodamine (TAMRA), Black Hole Question (BHQ) dyes and the like.

In some embodiments, quantitative assays are employed. In some such embodiments, an internal standard is employed in the reaction. Such internal standards generally comprise a control target nucleic acid sequence and a control polynucleotide probe. The internal standard can optionally further include an additional pair of primers. The primary sequence of these control primers may be unrelated to the MTB polynucleotides and specific for the control target nucleic acid sequence. Alternatively, no additional primer need be used if the control target sequence is designed such that it binds the MTB primers. The amount of target nucleic acid in a test sample can be quantified using "end point" methods or "real time" methods.

In some embodiments, MTB detection assays are provided as high-throughput assays. For high-throughput assays, reaction components are usually housed in a multi-container carrier or platform, such as a multi-well microtiter plate, which allows a plurality of assay reactions containing different test samples to be monitored in the same assay. In some embodiments, highly automated high-throughput assays are employed to increase the efficiency of the screening or assay process. Many high-throughput screening or assay systems are now available commercially, as are automation capabilities for many procedures such as sample and reagent pipetting, liquid dispensing, timed incubations, formatting samples into microarrays, microplate thermocycling and microplate readings in an appropriate detector, resulting in much faster throughput times. In some embodiments, reactions are performed in microfluidic devices (e.g., cards).

The polynucleotides, methods, and kits are useful in clinical or research settings for the detection and/or quantitation of MTB nucleic acids. Thus, in these settings the polynucleotides can be used in assays to diagnose MTB infection in a subject, or to monitor the quantity of an MTB target nucleic acid sequence in a subject infected with MTB. Monitoring the quantity of bacteria in a subject is particularly important in identifying or monitoring response to anti-bacterial therapy.

In some embodiments, a dual target assay is performed using real-time PCR, combined with sample inactivation. While a variety of sample may be used, highly clinically relevant sample include smear positive or smear negative specimens of sputum (induced or expectorated), bronchoalveolar lavage (BAL) samples, or N-Acetyl-LCysteine (NALC)-treated sediments of sputum and BAL samples. Challenges presented with these samples include the molecular complexity of sputum, which contains numerous components that can interfere with molecular assays, cell lysis, and cell inactivation.

In some embodiments, a sample inactivation step is performed to reduce the infection risk associated with clinical specimens that may contain MTB. Reduction of infection risk is achieved, for example, by incubating clinical samples with inactivation reagent (see Example 3, below).

In some embodiments, the assays are amenable for use with automated real-time PCR detection system, such as the Abbott m2000sp system. Thus, in some embodiments, prior to conducting an assay, the samples are prepared for use with such systems. For example, in some embodiments, preparation of target DNA is performed using a magnetic microparticle-based technology (Abbott mSample Preparation SystemDNA). This can be performed using an Abbott m2000sp for automated sample preparation or using a manual sample preparation protocol. In some embodiments, an internal control (IC), positive control, and negative control are processed from the start of sample preparation to demonstrate that the process has proceeded correctly.

For amplification, in some embodiments, purified sample DNA and master mix are added to a 96-well PCR plate using an Abbott m2000sp instrument or manually. After addition, each plate is sealed and transferred to an Abbott m2000rt where PCR amplification is performed using DNA Polymerase.

In some embodiments, the presence of MTB amplification products is detected during the annealing/extension step by measuring the real-time fluorescence signal of the MTB probes. The presence of IC amplification products is detected by measuring the real-time fluorescence signal of the IC probe. In some embodiments, the MTB and IC probes are single-stranded DNA oligonucleotides consisting of the target-specific binding sequence, a fluorescent moiety covalently linked to the 5' end of the probe, and a quenching moiety covalently linked to the 3' end of the probe. In the absence of the MTB or IC target sequences, probe fluorescence is quenched. In the presence of MTB or IC target sequences, the MTB or IC probes specifically bind to their complementary sequences in the targets during the annealing/extension step, allowing fluorescent emission and detection. In some embodiments, the MTB probes are labeled with different fluorescent dyes (FAM™ for MTB target probes, Quasar® for IC), thus allowing the amplification products of MTB and IC to be simultaneously detected in the same reaction.

In some embodiments, steps are taken to avoid nucleic acid contamination. For example, in some embodiments, contamination is minimized because: PCR amplification and oligonucleotide hybridization occur in a sealed multi-well plates; detection is carried out automatically without the need to open the reaction vessels (e.g., plate wells); aerosol barrier pipette tips are used for all pipetting; the pipette tips are discarded after use; and separate dedicated areas are used to perform the MTB assay.

In some embodiments, the above reagents are provided in the form of a kit and/or system (e.g., systems comprising automated sample handling and assay instruments described herein). For example, in some embodiments, the kit comprises, consists essentially of, or consists of:

1. MTB Internal Control (4 vials, 0.4 mL per vial)<0.01% noninfectious linearized DNA plasmid in a buffer solution with carrier DNA. Preservatives: Sodium azide and 0.15% ProClin® 950.
2. Amplification Reagent Pack (4 packs, 24 tests/pack). Each Reagent Pack contains: 1 bottle (0.078 mL) DNA Polymerase (5.4 to 5.9 units/µL) in buffered solution with stabilizers. 1 bottle (0.5314 mL) MTB Amplification Reagent. <0.1% synthetic oligonucleotides (one or more target primer sets and probes; a primer set and probe for the internal control), and <0.6% dNTPs in a buffered solution with a reference dye. Preservatives: Sodium azide and 0.15% ProClin® 950. 1 bottle (0.778 mL) Activation Reagent. 38 mM magnesium chloride in a buffered solution. Preservatives: Sodium azide and 0.15% ProClin® 950.
3. MTB Negative Control (8 vials, 1.6 mL per vial); Buffered solutions; Preservatives: Sodium azide and 0.15% ProClin® 950.
4. MTB Positive Control (8 vials, 1.6 mL per vial); <0.01% noninfectious linearized DNA plasmid in a buffer solution with carrier DNA. Preservatives: Sodium azide and 0.15% ProClin® 950.

In some embodiments, all forms of MTB are detected (e.g., the primers and probes are selected to identify all MTB nucleic target sequences that might be present in a sample). In some embodiments, specific MTB sequences are detected, such as antibiotic-resistant strains (e.g., rifampicin, isoniazid).

EXAMPLES

The following examples are for illustrative purposes only and should not be construed to limit the scope of this invention in any way.

Example 1

Exemplary Assay Workflow

This example describes a specific, efficient approach to conducting real-time PCR to detect MTB in a sample. In some embodiments, real-time PCR methods comprise or consist of the following steps:
1. Inactivation of MTB in samples (e.g., sputum, bronchoalveolar lavage [BAL], and N-acetyl-L-cysteine [NALC] sediments of sputum and BAL) using an inactivation reagent (IR). In some embodiments, the inactivation reagent comprises or consists isopropanol, sodium hydroxide, TWEEN-20, and water;
2. Sample preparation in which DNA is extracted from the inactivated samples using reagents; sample preparation is performed using the automated m2000sp instrument (Abbott Molecular), or manually;
3. PCR assembly in which purified samples and assay PCR components are added together in a 96-well optical reaction plate or other multi-chamber reaction support; this is performed using the m2000sp or manually;
4. Manual sealing of the 96-well optical reaction plate and transfer of the plate to an m2000rt instrument.
5. Amplification and detection of PCR products using the automated m2000rt instrument; patient results are automatically reported on the m2000rt workstation. A graphical summary of this workflow is shown in FIG. 1.

Example 2

Target Selection and Primer/Probe Design

In some embodiments, a dual target strategy is employed for detecting MTB complex. The two targets include: Insertion sequence (IS) 6110 and Protein Antigen B (PAB). See Table 1 below:

TABLE 1

Abbott RealTime MTB target selection:

| IS6110 | Insertion sequence (IS) of the IS3 category<br>Usually present in multiple copies per cell<br>(e.g. Denmark, 50% 11-15 copies per cell)<br>Some TB strains have no or low copy numbers of IS6110 |
|---|---|
| PAB | Single copy gene coding for protein antigen b |

Used of a dual target strategy prevents false negative results caused by target sequences mutation or deletion.

Probes and primers that find use in the detection of IS6110 and PAB target sequences include those in Table 2.

TABLE 2

RealTime MTB primer/probe sequences:

| Material | SEQ ID NO | Sequence |
|---|---|---|
| IS6110 (121) FP | SEQ ID NO: 1 | 5' CCT GCG AGC GTA GGC GTC GGT GA 3' |
| IS6110 (121) RP | SEQ ID NO: 2 | 5' CGT CCA GCG CCG CTT CGG ACC A 3' |
| PAB abt2 FPb | SEQ ID NO: 3 | 5' GCA CCT CAA GCT GAA CGG AAA AGT CCT 3' |
| PAB abt2 RPx | SEQ ID NO: 4 | 5' CCG GGG TTG AGC GCA GCG ATC T 3' |
| IS6110 probe6 | SEQ ID NO: 5 | 5' 6-Fam-pdU#AG GpdUG AGG pdUpdC*pdU GpdCpdU ApdCpdC pdC-BHQ1 dT 3' |

TABLE 2-continued

RealTime MTB primer/probe sequences:

| Material | SEQ ID NO | Sequence |
|---|---|---|
| PAB probe 1 | SEQ ID NO: 6 | 5' 6-Fam-pdUApdC pdCAG GGpdC ApdCpdC ApdUpdC AAA-BHQ1 dT 3' |
| IC FP 196 | SEQ ID NO: 7 | 5' CTA CAG CAG AGT TGG CAG CTT CAC TTT C 3' |
| IC RP 310 | SEQ ID NO: 8 | 5' GTC TGG CCT TTC AGC AAG TTT C 3' |
| Internal Control Probe: | SEQ ID NO: 9 | 5' Quasar-GApdC GAG pdUpdUpdC ApdUG AGG GpdCA-BHQ2 dT 3' |

(FP = forward primer; RP = reverse primer; #pdU = 5' propynyl dU; *pdC = 5' propynyl dC; Fam = fluorescein dye; BHQ = Black Hole Quencher; IC = internal control)

Table 3 provides alternative primers and probes for use in the detection MTB target sequences. In addition to IS6110 and PAB, additional targets include rPOB (single copy gene coding for β subunit of RNA polymerase, site of about 95% of rifampicin-resistance mutations), SenX3-RegXe (single copy gene coding for regulatory proteins), hsp65 (single copy gene coding for heat shock protein), and MPB64 (single copy gene coding for 23 KDA protein). Table 3. Other primer/probe sequences:

| Name | SEQ ID NO | Sequences |
|---|---|---|
| IS6110 (104) FP1 | SEQ ID NO: 10 | 5' GCCGCTTCGGACC ACCAGCACCTAAC |
| IS6110 (104) RP1 | SEQ ID NO: 11 | 5' GTAGGCGTCGGTG ACAAAGGCCACGTAG |
| IS6110 (104) probe | SEQ ID NO: 12 | 5' TGCCCAGGTCGAC ACATA |
| IS6110 (80) FP1 | SEQ ID NO: 13 | 5' TACGACCACATCA ACCGGGAGCCCA |
| IS6110 (80) RP1 | SEQ ID NO: 14 | 5' GCGTGGACGCGGC TGATGTGCTCCT |
| IS6110 (80) pr1 | SEQ ID NO: 15 | 5' CCGCGAGCTGCGC GATG |
| PAB abt1 FP | SEQ ID NO: 16 | 5'-GCACGCTGCTCTA CCCGCTGTTCAACCT |
| PAB abt1 RP | SEQ ID NO: 17 | 5'-GTGCCCTGAGCGG TGATCGTGACGTT |
| PAB abt1 Probe: | SEQ ID NO: 18 | 5' TCCGGCCTTTCAC GAGA |
| nhsp65 FP1 | SEQ ID NO: 19 | 5' TCGGGGCTCGGGT AGAAGTT |
| nhsp65 RP1 | SEQ ID NO: 20 | 5' TCGTCAACTCGGG CAGCAAC |
| nhsp65 probe 1 | SEQ ID NO: 21 | 5' TACTCGGCTCACG CACG |
| vhsp65 FP1 | SEQ ID NO: 22 | 5' GGCTCGGGTAGAA GTTCGACTTGG |
| vhsp65 RP1 | SEQ ID NO: 23 | 5' GTCAACTCGGGCA GCAACGAC |

-continued

| Name | SEQ ID NO | Sequences |
|---|---|---|
| vhsp65 probe 1 | SEQ ID NO: 24 | 5' CTCACGCACGGCG GTATTC |
| senX3 FP | SEQ ID NO: 25 | 5' GGCAGCGGACTCG GGTT |
| senX3 RP | SEQ ID NO: 26 | 5' ACCGCAGTTCGGG CTCTC |
| senX3 Pr | SEQ ID NO: 27 | 5' TCACGACGACGAG CGAC |
| regX3 FP | SEQ ID NO: 28 | 5' CGCTGATGACCAG TGTGTTGATT |
| regX3 RP | SEQ ID NO: 29 | 5' GCAGCATCAGATC GAGCAGGAC |
| regX3 Probe | SEQ ID NO: 30 | 5' ATGGTCCGGCAGC TCTC |
| MPB64 FP1 | SEQ ID NO: 31 | 5' CAACATCAGCCTG CCCAGTTACTACC |
| MPB64 RP1 | SEQ ID NO: 32 | 5' CTTCGCGTGGAGT GGACGATG |
| MPB64 Probe1 | SEQ ID NO: 33 | 5' AAGTCGCTGGAAA ATTACAT |
| rPOB FPa | SEQ ID NO: 34 | 5' CGTGGAGGCGATC ACACCGCAGACGTT |
| rPOB RPb | SEQ ID NO: 35 | 5' CGTTGATCAACAT CCGGCCGGTGGTC |
| rPOB probe5 | SEQ ID NO: 36 | 5' CGGTCTGTCACGT GAGCGTGC |

Example 3

Sample Inactivation

This example describes exemplary reagents and methods for conducting a sample inactivation step.
Preparation of Inactivation Reagent (IR)
 Materials Employed:
 Polypropylene or glass container
 10M NaOH
 Isopropanol
 TWEEN-20
 Purified water
 Preparation of IR:
 Material Volume Required for 500 mL
  10M NaOH 20 mL
  Purified water 179.1 mL
  Isopropanol 300 mL
  TWEEN-20 0.9 mL
1. Add 179.1 mL of water to an empty polypropylene or glass container (avoid use of a polystyrene container).
2. Add 0.9 mL of TWEEN-20 to the container.
3. Add 20 mL of 10M NaOH to the container.
4. Add 300 mL of isopropanol to the container.
5. Mix the components by inversion 20 times.
Use or store at ambient temperature for up to 1 month.
Inactivation Procedure:
 1. If frozen, thaw specimens at 15 to 30° C.
 2. Estimate the volume of specimen to be inactivated.
 3. Add IR at a ratio of 1:3 (e.g., 1 mL specimen+3 mL IR) (the preferred specimen volume is 0.3 to 10 mL).
 4. Invert the container to ensure contact between the IR and the specimen.
 5. Vortex the mixture for 20 to 30 seconds.
 6. Incubate the mixture at ambient temperature for at least 1 hour and preferably no more than 24 hours. Vortex the mixture one final time for 20 to 30 seconds at 20 to 30 minutes into the incubation period.

Example 4

Sample Preparation Method

The MTB assay of Example 1 uses an Abbott automated m2000sp instrument or manual method for processing sputum, BAL and NALC-NaOH sediment of sputum or BAL samples and uses an Abbott automated m2000rt instrument for amplification and detection. Both processes entail DNA extraction from samples, both DNA purifications are performed using the DNA GPR (List 6K12-24) sample preparation reagents from the Abbott mSample Preparation System$_{DNA}$.

The sample preparation reagents and method (including lyses step, wash step, elution step, tip reuse arrangement etc.) were optimized to reduce the inhibitory effect on PCR reactions due to the inhibitory sputum or carryover of TB Inactivation reagent (IR): thus centrifugation to get rid of IR in the IR treated sample is not necessary. The procedure is also optimized to reduce carryover from high positives to nearby negative sample. The sample preparation is also optimized to ensure TB cell breakage for efficient DNA recovery and PCR.
Real-Time PCR:

After PCR reaction assembly in a 96-well optical reaction plate (either manually or via the m2000sp), the 96-well plate is manually sealed and transferred to the m2000rt to perform the amplification and real-time fluorescence detection reaction. Patient results are automatically reported on the m2000rt workstation. The MTB assay detects an internal control nucleic acid sequence as sample validity control, sample extraction and amplification efficiency control. Table 4 provides exemplary PCR cycling conditions.

TABLE 4

| Stage | Cycle | Step | Temperature (° C.) | Time |
|---|---|---|---|---|
| 1 | 1 | 1 | 50 | 10 min |
| 2 | 1 | 1 | 94 | 10 min |
| 3 | 50 | 1 | 94 | 35 sec |
|  |  | 2 | 64 | 15 sec |
| Read |  | 3 | 65 | 40 sec |

For the data shown in the below examples, an assay cutoff of 42 was used. That is samples with Ct values<42 are considered to be MTB Detected, while samples with assay Ct values>42 are considered MTB Not Detected.

Assays run on the m2000rt are per the manufacturer's recommend protocols. One such example includes the steps of:
 1. 96 IR-treated samples are performed per run. One negative control and 1 positive control are included in each run, therefore allowing a maximum of 94 IR-treated samples to be processed per run.
 2. Before use, vortex IR-treated samples for 3 to 5 seconds. Using a pipette, transfer the IR-treated samples to the reaction vessels. Minimize the transfer of visible particulates in the IR-treated samples during this step.

3. Thaw assay controls, IC, and amplification reagents at 2 to 8° C. or 15 to 30° C. Once thawed, IC can be stored closed at 2 to 8° C. for up to 14 days prior to use. Once thawed, controls can be stored at 2 to 8° C. for up to 24 hours prior to use. If not using the optional amplification reagent extended use feature: Thaw new amplification reagents at 2 to 8° C. or 15 to 30° C. Once thawed, the amplification reagents can be stored at 2 to 8° C. for up to 24 hours, prior to use. If using the optional amplification reagent extended use feature: Select new and/or partial amplification reagent packs to be used in the run. Refer to Abbott m2000sp Operations Manual (List No. 9K20-06 or higher), Operating Instructions, for instructions pertaining to amplification reagent pack inventory management. Amplification reagent packs should have the same lot number.

4. Vortex each control 3 times for 2 to 3 seconds each time before use. Ensure that bubbles or foam are not created. If found, remove them with a new sterile pipette tip for each tube. Ensure that the contents of each vial are at the bottom after vortexing by tapping the vials on the bench to bring liquid to the bottom of the vial.

5. Gently invert the Abbott mSample Preparation SystemDNA bottles to ensure a homogeneous solution. If crystals are observed in any of the reagent bottles upon opening, allow the reagent to equilibrate at room temperature until the crystals disappear. Do not use the reagents until the crystals have dissolved. Ensure bubbles or foam are not generated; if present, remove with a sterile pipette tip, using a new tip for each bottle. NOTE: Before pouring the mMicroparticlesDNA into the 200 mL reagent vessel, vigorously mix or vortex until the mMicroparticlesDNA are fully resuspended.

6. Vortex the IC vial 3 times for 2 to 3 seconds each time before use. Ensure bubbles or foam are not generated; if present, remove with a sterile pipette tip.

7. Using a calibrated precision pipette dedicated for internal control use only, add 180 µL of IC to 1 bottle of mLysisDNA buffer. Mix by gently inverting the container 5 to 10 times to minimize foaming. Each bottle of mLysisDNA buffer supports up to 48 sample preparations. Add 180 µL of IC to a second bottle of mLysisDNA buffer for 49 to 96 samples. If using the optional amplification reagent extended use feature, partial vials of IC can be recapped and stored at 2 to 8° C. for a second use.

8. Add 25 mL of USP grade 190 to 200 proof ethanol (95 to 100% ethanol) to the mLysisDNA buffer+IC reagent bottle. Do not use ethanol that contains denaturants. Gently invert the container to ensure homogeneous solution. For 49 to 96 samples, add 25 mL of ethanol to a second bottle of mLysisDNA buffer+IC. Gently invert to ensure a homogeneous solution.

9. Add 70 mL USP grade 190 to 200 proof ethanol (95 to 100% ethanol) to mWash 2DNA bottle. Do not use ethanol that contains denaturants. Each bottle of mWash 2DNA supports up to 48 reactions. Gently invert to ensure a homogeneous solution.

10. Place the negative and positive control and the patient specimens into the Abbott m2000sp sample rack.

11. Place the 5 mL Reaction Vessels into the Abbott m2000sp 1 mL subsystem carrier.

12. Load the carrier racks containing the Abbott mSample Preparation SystemDNA reagents and the Abbott 96-Deep-Well Plate on the Abbott m2000sp worktable as described in the Abbott m2000sp Operations Manual, Operating Instructions.

13. From the Run Sample Extraction screen, select and initiate the sample extraction protocol as described in the Abbott m2000sp Operations Manual, Operating Instruction. NOTE: Change gloves before handling the amplification reagents.

14. Load the amplification reagent pack and master mix vial (if needed) on the Abbott m2000sp worktable after sample preparation is completed. Each amplification reagent pack supports up to 24 reactions. Thaw 1 set of reagents for 1 to 24 samples, 2 sets for 25 to 48 samples, 3 sets for 49 to 72 samples and 4 sets for 73 to 96 samples. Ensure the amplification reagents are thoroughly thawed before use. Ensure that the contents are at the bottom of the vials by tapping the vials in an upright position on the bench. Remove the amplification reagent vial caps. If using the optional amplification reagent extended use feature, a combination of new and partial reagent packs may be used. If not using the optional amplification reagent extended use feature, only new reagent packs may be used. Ensure that the contents of new amplification reagent packs are at the bottom of the vials prior to opening the amplification reagents by tapping the vials in an upright position on the bench. Do not tap partial amplification reagent packs being used a second time. Tapping may result in loss of master mix volume in the cap. Remove caps. If a new amplification reagent pack is stored for a second use, the vials are recapped for storage. If planning to reuse the original caps to recap the reagent vials, the original caps are saved and used. If planning to use fresh caps to recap the reagent vials, original caps are discarded. Partial amplification packs are loaded to the left of new amplification packs on the Abbott m2000sp worktable. Ensure that the amplification reagent packs are firmly seated on the instrument.

15. Select the appropriate deep-well plate from the Run Master Mix Addition screen that matches the corresponding sample preparation extraction. Initiate the Abbott m2000sp Master Mix Addition protocol. Follow the instructions as described in the Abbott m2000sp Operations Manual, Operating Instructions section. NOTE: The assembly of the amplification master mix and sample eluates into the Abbott 96-Well Optical Reaction Plate (step 15) should be initiated within 1 hour after completion of Sample Preparation. NOTE: The Abbott m2000rt protocol (step 20) should be started within 90 minutes of the initiation of the Master Mix Addition protocol. NOTE: If the run is aborted for any reason subsequent to step 15, the amplification reagents are to be discarded and a new 96-well PCR plate should be used if the Abbott m2000sp Master Mix Addition Protocol (step 15) will be repeated.

16. Switch on and initialize the Abbott m2000rt in the Amplification Area. NOTE: The Abbott m2000rt requires 15 minutes to warm up. NOTE: Change laboratory coats and gloves before returning to the sample preparation area.

17. Place the Abbott 96-Well Optical Reaction Plate into the Abbott Splash-Free Support Base after the Abbott m2000sp instrument has completed addition of samples and master mix.

18. Seal the Abbott 96-Well Optical Reaction Plate according to the Abbott m2000sp Operations Manual, Operating Instructions section. Export the completed PCR plate results to a CD (or directly to a mapped Abbott m2000rt via a network connection).

In some embodiments, a manual sample preparation method is employed. An example of such a method is as follows:

1. Thaw amplification reagents at 15 to 30° C. or at 2 to 8° C. This step can be initiated before completion of the sample preparation procedure.

2. 12 samples are processed per set of magnetic racks. A negative control and a positive control are included in each run, therefore allowing a maximum of 10 specimens to be processed. Prepare the specimens for processing by following these steps: NOTE: Patient specimens should be inactivated prior to beginning sample extraction.

3. Thaw 1 tube of the MTB Negative Control, 1 tube of MTB Positive Control, and 1 vial of MTB Internal Control at 15 to 30° C. or at 2 to 8° C. Once thawed, if IC is not being processed immediately, store at 2 to 8° C. for up to 14 days prior to use. Once thawed, if controls are not being processed immediately, store at 2 to 8° C. for up to 24 hours prior to use. Vortex controls and IC 3 times for 2 to 3 seconds each time before use. Ensure that the contents of each vial are at the bottom after vortexing by tapping the vials on the bench to bring liquid to the bottom of the vial. Ensure bubbles or foam are not generated; if present, remove with a sterile pipette tip, using a new tip for each vial.

4. Open the Abbott mSample Preparation SystemDNA reagent pack(s). If crystals are observed in any of the reagent bottles upon opening, allow the reagent to equilibrate at room temperature until the crystals disappear. Do not use the reagents until the crystals have dissolved.

5. Prepare the mWash 2DNA by adding 70 mL of USP grade 190 to 200 proof ethanol (95 to 100% ethanol) to the mWash 2DNA bottle. Do not use ethanol that contains denaturants. Gently invert to ensure a homogeneous solution. NOTE: Mark the mWash 2DNA bottle to indicate that ethanol has already been added for extended use.

6. Prepare the mLysisDNA by adding 25 mL of USP grade 190 to 200 proof ethanol (95 to 100% ethanol) to the mLysisDNA bottle. Do not use ethanol that contains denaturants. Gently invert 5 to 10 times to mix and to minimize foaming. NOTE: Mark the mLysisDNA bottle to indicate that ethanol has already been added for extended use.

7. Calculate the volume of mLysisDNA solution required for the manual run: (1.85 mL of mLysisDNA×number of samples). Pipette the required volume of mLysisDNA solution into a polypropylene container large enough to hold the entire volume. Calculate the volume of IC required for the manual run: (3.51 µL of IC×number of samples). Use a precision pipette dedicated to internal control use only to add the required volume of IC into the polypropylene container containing the mLysisDNA solution required for the manual run. Mix mLysisDNA solution and IC mixture by gentle inversion 10 to 15 times to minimize foaming. After initial use, partial IC vials maybe stored at 2 to 8° C. for up to 14 days and used 1 additional time.

8. Gently invert all the reagent bottles, except the mMicroparticlesDNA bottle and the mWash 1DNA bottle, 5 to 10 times to ensure a homogenous solution prior to use. The mMicroparticlesDNA bottle will be mixed in step 11.

9. Turn on the temperature-controlled dry heating blocks. Set the first block to 58° C. Set the second block to 80° C. NOTE: Check the temperature of the heating blocks. Do not proceed until the heating blocks are at the correct temperature.

10. Label all necessary tubes: One 5 mL reaction vessel per sample for the Lysis Incubation and mWash 1DNA steps. One 1.5 mL microfuge tube per sample for the first and second mWash 2DNA and Elution steps. One 1.5 mL microfuge tube per sample or a 96-well polypropylene plate for the eluate.

11. Place the labeled 5 mL reaction vessels for each sample in unheated stand. Resuspend mMicroparticlesDNA by vortexing or vigorously shaking until particles are in suspension and settled particles are no longer seen on the bottom of the bottle. After the particles are resuspended, use a precision pipettor and a sterile 200 µL aerosol barrier pipette tip to add 50 µL of mMicroparticlesDNA to each reaction vessel.

12. Using a fresh, sterile 1000 µL aerosol barrier pipette tip for each sample, add 1.75 mL (2×875 µL) of mLysisDNA to the reaction vessels.

13. Add 0.8 mL of the controls, and specimens to the appropriate reaction vessels using a precision pipettor and a fresh, sterile 1000 µL aerosol barrier pipette tip for each sample. Mix each sample/mLysisDNA mixture by aspirating and dispensing the 800 µL volume 5 to 10 times until a uniform suspension is obtained. NOTE: Aspirate and dispense liquid slowly to avoid foaming.

14. Transfer the 5 mL reaction vessels into the 58° C. heating block.

15. Start the timer and incubate for 15 minutes.

16. After incubation using a fresh, sterile 1000 µL aerosol barrier pipette tip for each sample, mix the mixture 5 times by aspirating and dispensing 800 µL.

17. Start the timer and incubate for an additional 10 minutes in the 58° C. heating block.

18. After incubation using a fresh, sterile 1000 µL aerosol barrier pipette tip for each sample, mix the mixture 5 times by aspirating and dispensing 800 µL.

19. Start the timer and incubate for an additional 10 minutes in the 58° C. heating block.

20. After the incubation is complete, place the reaction vessels in a magnetic capture stand for 2 minutes to allow the particles to be captured on the side of the reaction vessels.

21. With the reaction vessels in the magnetic capture stand, use a fresh, sterile 1000 µL aerosol barrier pipette tip or disposable transfer pipette for each sample to carefully remove the mLysisDNA from each reaction vessel and discard the fluid into a liquid waste container. Remove the fluid as completely as possible. Do not disturb or aspirate the captured magnetic particles.

22. Remove the reaction vessels from the magnetic rack and transfer to a nonmagnetic rack. mWash 1DNA (Wash).

23. Using a precision pipettor and a fresh, sterile 1000 µL aerosol barrier pipette tip for each sample, add 800 µL of mWash 1DNA to the samples and resuspend the magnetic particles in the wash fluid by gently mixing 10 times by aspiration and dispense with a pipette tip. Wash the particles from the side of the reaction vessel, if necessary. NOTE: When adding mWash 1DNA wash, dispense liquid slowly to avoid splashing.

24. Transfer the wash fluid and particles to a labeled 1.5 mL microfuge tube.

25. Place the tubes in a magnetic capture stand for 1 minute to allow the particles to be captured on the side of the tubes.

26. With the tubes in the magnetic capture stand, use a fresh, sterile 1000 µL aerosol barrier pipette tip for each sample to carefully remove the mWash 1DNA from each tube and discard fluid into a liquid waste container. Remove the fluid as completely as possible. DO NOT disturb or aspirate the captured magnetic particles.

27. Remove the tubes from the magnetic rack and transfer to a nonmagnetic rack. mWash 2DNA (First Wash).

28. Using a precision pipettor and a fresh, sterile 1000 µL aerosol barrier pipette tip for each sample, add 800 µL of mWash 2DNA to the samples and resuspend the magnetic particles in the wash fluid by gently mixing 5 to 10 times by aspiration and dispense with a pipette tip. Wash the particles from the side of the tube, if necessary. NOTE: When adding mWash 2DNA wash, dispense liquid slowly to avoid splashing.

29. Place the tubes in a magnetic capture stand for 1 minute to allow the particles to be captured on the side of the tubes.

30. With the tubes in the magnetic capture stand, use a fresh, sterile 1000 µL aerosol barrier pipette tip for each sample to carefully remove the mWash 2DNA from each tube and discard fluid into a liquid waste container. Remove the fluid as completely as possible. DO NOT disturb or aspirate the captured magnetic particles.

31. Remove the tubes from the magnetic rack and transfer to a nonmagnetic rack. mWash 2DNA (Second Wash).

32. Using a precision pipettor and a fresh, sterile 1000 µL aerosol barrier pipette tip for each sample, add 800 µL of mWash 2DNA to the samples and resuspend the magnetic particles in the wash fluid by gently mixing 5 to 10 times by aspiration and dispense with a pipette tip. Wash the particles from the side of the tube, if necessary. NOTE: When adding mWash 2DNA wash, dispense liquid slowly to avoid splashing.

33. Place the tubes in a magnetic capture stand for 1 minute to allow the particles to be captured on the side of the tubes.

34. With the tubes in the magnetic capture stand, use a fresh, sterile 1000 µL aerosol barrier pipette tip for each sample to carefully remove the mWash 2DNA from each tube and discard fluid into a liquid waste container. Remove the fluid as completely as possible. DO NOT disturb or aspirate the captured magnetic particles.

35. Remove the tubes from the magnetic rack and transfer to the 80° C. heating block and incubate for 15 minutes with caps open to allow for the evaporation of the ethanol.

36. Using a precision pipettor and a fresh, sterile 1000 µL aerosol barrier pipette tip for each sample, add 250 µL of mElution BufferDNA to the samples and resuspend the magnetic particles in the fluid by aspiration and dispense with the pipette tip. Wash the particles from the side of the tube, if necessary.

37. Place the tubes in the 80° C. heating block, start the timer, and incubate for 4 minutes.

38. Remove the tubes from the 80° C. heating block. Using a fresh, sterile 1000 µL aerosol barrier pipette tip for each sample, mix the sample and mElution BufferDNA mixture 4 times by aspirating and dispensing 200 µL.

39. Return the tubes to the 80° C. heating block. Start the timer and incubate for 4 minutes.

40. Remove the tubes from the 80° C. heating block and place in a magnetic capture stand for 1 minute to allow the particles to be captured on the side of the tubes.

41. With the tubes in the magnetic capture stand, use a fresh, sterile 1000 µL aerosol barrier pipette tip for each sample to carefully remove the eluted sample from the tubes. Do not disturb or aspirate the captured microparticles. The eluted sample(s) can be placed into a fresh, labeled 1.5 mL microfuge tube or a 96-well polypropylene plate. NOTE: The assembly of the amplification master mix and sample eluates into the Abbott 96-Well Optical Reaction Plate (step 48) must be initiated within 1 hour after completion of Sample Preparation.

42. Switch on and initialize the Abbott m2000rt instrument. NOTE: The Abbott m2000rt requires 15 minutes to warm up.

43. Create the Abbott m2000rt test order. Refer to the Operating Instructions section of the Abbott m2000rt Operations Manual. From the Protocol screen, select the Abbott RealTime MTB assay application protocol. NOTE: Remove gloves before returning to the reagent preparation area.

44. Prepare the amplification master mix. NOTE: All reagent preparation should take place in the dedicated Reagent Preparation Area. Change gloves before handling the amplification reagents. Do not vortex or invert the amplification reagent pack. Each amplification reagent pack supports up to 24 reactions. Ensure the amplification reagents are thoroughly thawed before use. Prior to opening the amplification reagents, ensure that the contents of the amplification reagent pack are at the bottom by tapping the amplification reagent pack in an upright position on the bench to bring the liquid to the bottom of the vials. Identify the amplification reagents as follows: Activation Reagent (Reagent 1); MTB Amplification Reagent (Reagent 2); DNA Polymerase (Reagent 3); Remove and discard caps. Using a calibrated precision pipette dedicated for reagent use only, add 298 µL of Activation Reagent (Reagent 1) and 418 µL of MTB Amplification Reagent (Reagent 2) to the DNA Polymerase bottle (Reagent 3) to make master mix. Mix by gently pipetting up and down 5 times. Avoid creating foam.

45. Pipette the contents of the master mix from the DNA Polymerase bottle into a 1.5 mL microfuge tube (List No. 4J71-50 or equivalent). Mix by gently pipetting up and down 5 times. Avoid creating foam.

46. Place an Abbott 96-Well Optical Reaction Plate in the Abbott Splash-Free Support Base to prevent contamination. Contamination of the bottom of the Abbott 96-Well Optical Reaction Plate with fluorescent materials could potentially interfere with the MTB assay. The Abbott 96-Well Optical Reaction Plate should be held and transported with the Abbott Splash-Free Support Base to minimize contamination.

47. Using a precision pipette dedicated for reagent use only, dispense 25 µL aliquots of the amplification master mix into each well of the Abbott 96-Well Optical Reaction Plate that will be used to run the samples and controls. A calibrated repeat pipettor may be used. Add the master mix in an order starting with column 1 (from top to bottom), and moving to each consecutive column from left to right. Visually verify that 25 µL has been dispensed into each well. Transfer the Abbott 96-Well Optical Reaction Plate in the Abbott Splash-Free Support Base to the Sample Preparation Area.

48. Using a precision pipettor and a fresh, sterile 200 µL aerosol barrier pipette tip for each sample, transfer 25 µL of each eluted sample to the Abbott 96-Well Optical Reaction Plate. During the transfer of each sample, mix the final reaction by pipetting up and down 3 to 5 times. Visually verify that a total of 50 µL has been dispensed into each well.

49. Seal the Abbott 96-Well Optical Reaction Plate according to the instructions in the Abbott m2000rt Operations Manual, Operating Instructions section.

50. Centrifuge the Abbott 96-Well Optical Reaction Plate in the Abbott Splash-Free Support Base at 5000 g for 5 minutes.

51. Transfer the Abbott 96-Well Optical Reaction Plate in the Abbott Splash-Free Support Base to the Amplification Area. NOTE: The Abbott m2000rt protocol (step 52) should be started within 90 minutes following the initiation of the master mix addition and PCR plate preparation (step 44).

52. Place the Abbott 96-Well Optical Reaction Plate in the Abbott m2000rt instrument, select the test order created (step 43), and initiate the Abbott RealTime MTB assay application protocol, as described in the Abbott m2000rt Operations Manual, Operating Instructions section. At the completion of the run, assay results are reported on the Abbott m2000rt.

Example 5

Experimental Data—Inactivation

The IR TB killing effectiveness was evaluated. In this experiment, MTB-containing samples (cultured MTB that was diluted to known MTB concentrations prior to inactivation, as well as MTB-containing NALC-NaOH sediments) were subjected to the inactivation procedure of Example 3. Following inactivation, excess Inactivation Reagent was removed by centrifugation/washing and the surviving cells were placed into MGIT culture for up to 42 days or six weeks. This duration is the recommended longest time for MTB culture; most MTB positive specimens will result in detectable culture growth within 20 days of initiation of culture). Table 5 below illustrates the results obtained when testing the cultured samples following inactivation. The Positive Control (PC), which consists of non-inactivated MTB, demonstrated growth within the expected 20-day timeframe, while the Negative Control (NC), showed no growth.

TABLE 5

Inactivation of cultured high concentration MTB cells. Reduction of MTB Infection Risk Study Summary

| | | | Positive Samples Without IR Treatment | | Positive Samples With IR Treatment | |
|---|---|---|---|---|---|---|
| Study | Number of Isolate Samples | CFU/mL | Number Samples and Replicates Tested | Culture Positive | Number Samples and Replicates Tested | Culture Positive |
| 1 | 3[a] | $1 \times 10^8$ | 3 × 1 | 3 of 3 | 3 × 3 | 0 of 9 |
| | | $1 \times 10^7$ | 3 × 1 | 3 of 3 | 3 × 3 | 0 of 9 |
| | | $1 \times 10^6$ | 3 × 1 | 3 of 3 | 3 × 3 | 0 of 9 |
| 2 | 20[b] | N/A | 20 × 1 | 20 of 20 | 20 × 1 | 0 of 20 |
| 3 | 31[b] | N/A | 31 × 1 | 31 of 31 | 31 × 1 | 0 of 31 |

[a]Cultured Isolate Samples
[b]Clinical Isolate Samples

These data demonstrate the effectiveness of the inactivation procedure for inactivation of MTB.

Example 6

Analytical Inclusivity

Eight subspecies and 20 samples of MTB complex (*M. tuberculosis, M. africanum, M. bovis, M. bovis* BCG, *M. canettii, M. microti, M. caprae, M. pinnipedii.*) were obtained from ATCC (*M. canettii* was received from the Public Health Research Institute) and were tested from 10 to 100 genomic DNA copies/reaction (See Table 6). All 8 subspecies were detected at both levels.

TABLE 6

MTB complex subspecies tested

| Name | Name |
|---|---|
| *Mycobacterium tuberculosis* 25177D-5 (H37Ra) | *M pinnipedii* BAA-688D |
| | *M bovis* BCG 35747D |
| *M tuberculosis* 25618D-5 (H37Rv) | *M caprae* BAA-824D |
| *M microti* 11152 | *M tuberculosis* BAA-2236D |
| *M microti* 19422 | *M tuberculosis* BAA-2237D |
| *M africanum* 25420 | *M tuberculosis* 27294D |
| *M africanum* 35711 | *M tuberculosis* BAA-2234D |
| *M bovis* 35735 | *M tuberculosis* 35822D |
| *M bovis* 19274 | *M tuberculosis* 35838D |
| *M bovis* BCG 35746 | *M tuberculosis* BAA-2235D |
| *M canettii* | |

Forty six phylogenetically and geographically diverse MTB isolate DNAs (>50% with MDR) obtained from the Public Health Research Institute were tested from 25 to 100 genomic DNA copies/reaction (FIG. 2). All subspecies tested were detected.

Example 7

Analytical Specificity

Purified nucleic acid from different mycobacteria, viruses and other microorganisms (n=80) at targeted concentrations of 1e5 to 1e7 genomes/mL and cultured microorganisms at $1\times10^6$ cfu/mL were added to MTB negative control to evaluate the effect of potential cross-reactants on MTB assay results for MTB negative specimens. Purified nucleic acid from different mycobacteria, viruses and other microorganisms at targeted concentrations of $1\times10^6$ to $1\times10^7$ genomes per milliliter and cultured microorganisms at 1e6 cfu/mL were added to MTB positive samples to evaluate the effect of potential cross-reactants on MTB assay results for MTB positive specimens. MTB positive samples were prepared by diluting heat inactivated MTB cell stock in negative control to a targeted concentration of 1000 copies/mL (quantitated using a genomic DNA curve). None of the MTB negative samples tested with the potential cross-reactants was detected. All 80 MTB positive samples tested with potential cross-reactants were detected.

TABLE 7

Microorganisms tested to determine analytical specificity

| Species |
|---|
| *Mycobacterium abscessus* |
| *Mycobacterium austroafricanum* |
| *Mycobacterium avium* |
| *Mycobacterium avium* ssp. *avium* |
| *Mycobacterium avium* ssp. |
| *Mycobacterium celatum* |
| *Mycobacterium chelonae* |
| *Mycobacterium chitae* |
| *Mycobacterium fallax* |
| *Mycobacterium flavescens* |
| *Mycobacterium fortuitum* |
| *Mycobacterium gastri* |
| *Mycobacterium gordonae* |
| *Mycobacterium intracellulare* |
| *Mycobacterium kansasii* |
| *Mycobacterium lentiflavum* |
| *Mycobacterium marinum* |
| *Mycobacterium neoaurum* |
| *Mycobacterium* |
| *Mycobacterium phlei* |
| *Mycobacterium pneumoniae* |
| *Mycobacterium pulveris* |
| *Mycobacterium scrofulaceum* |

TABLE 7-continued Microorganisms tested to determine analytical specificity Species Mycobacterium shimoidei
Mycobacterium simiae
Mycobacterium smegmatis
Mycobacterium sphagni
Mycobacterium terrae
M. thermoresistibile
Mycobacterium tokaiense
Mycobacterium ulcerans
Mycobacterium vaccae
Mycobacterium xenopi
Acinetobacter baumannii
Aeromonas hydrophila
Bacillus cereus
Bacillus subtilis
Bordetella parapertussis
Campylobacter jejuni
Candida albicans
Chromobacterium violaceum
Chlamydia pneumoniae
Chlamydia trachomatis
Citrobacter freundii
Corynebacterium diptheriae
Corynebacterium xerosis
Cryptococcus neoformans
Cytomegalovirus
Enterobacter aerogenes
Enterobacter cloacae
Enterococcus faecalis
Enterococcus avium
Escherichia coli
Herpes simplex virus 1
Klebsiella pneumoniae
Lactobacillus delbrueckii
Legionella pneumophila
Neisseria gonorrhoeae
Neisseria meningitidis
Porphyromonas gingivalis
Proteus mirabilis
Pseudomonas aeruginosa
Salmonella choleraesuis
Serratia marcescens
Staphylococcus aureus
Staphylococcus epidermidis
Staphylococcus haemolyticus
Staphylococcus hominis
Streptococcus agalactiae
Streptococcus gordonae
Streptococcus mitis
Streptococcus mutans
Streptococcus pneumoniae
Streptococcus pyogenes
Streptomyces griseinus
Varicella-zoster virus
Veillonella parvula

Example 8

Analytical Sensitivity

A MTB panel, strain H37Rv at 40 cfu/mL was serially diluted in pooled MTB negative sputum to generate a sensitivity panel. Sixteen replicates of each dilution were tested. A detection rate of 100% was observed at all dilutions 160 fold and lower. Results are shown in Table 8.

TABLE 8

Analytical sensitivity determined by testing serial dilutions of a MTB panel.

| Series dilution | | AM RealTime MTB | |
| --- | --- | --- | --- |
| | | Ct cut off 42 | Ct cut off 39 |
| from 40 cfu/mL | Dil. Fold | Hit Rate | Hit Rate |
| 1 | 0 | 16/16 | 16/16 |
| 2 | 2 | 16/16 | 16/16 |
| 3 | 4 | 16/16 | 16/16 |
| 4 | 8 | 16/16 | 16/16 |
| 5 | 20 | 16/16 | 16/16 |
| 6 | 40 | 16/16 | 12/16 |
| 7 | 80 | 16/16 | 15/16 |
| 8 | 160 | 13/16 | 10/16 |
| 9 | 320 | 15/16 | 7/16 |
| 10 | 640 | 8/16 | 4/16 |
| 11 | 1278 | 4/16 | 0/16 |
| 12 | 2564 | 3/16 | 0/16 |
| 13 | 5128 | 1/16 | 0/16 |

Example 9

Clinical Specificity

Culture-negative NALC samples (n=155), sputum (n=23) and BAL (n=28) samples (NALC samples were from MTB suspect population. Sputum and BAL samples were from patients with no TB symptoms) were tested to determine clinical specificity (see data summarized in table 10 below). Specificity for sputum and BAL samples was 100%. Specificity for NALC samples was 98.7% with an overall specificity of 99%.

TABLE 9

Clinical specificity determined by testing TB negative samples.

| Specimen type | Specificity definition | Tested Numbers | Negative results | Positive results | Specificity |
| --- | --- | --- | --- | --- | --- |
| NALC | TB suspect Culture negative | 155 | 153 | 2 | 98.7% |
| Sputum | No TB symptom | 23 | 23 | 0 | 100% |
| BAL | No TB symptom | 28 | 28 | 0 | 100% |
| Total | | 206 | 204 | 2 | 99% |

TABLE 10

TB Culture positive samples (including both smear positives and negatives) were tested by MTB assay (AM) vs. another comparator assay (Comparator).

| TUBE # | SPECIMEN TYPE | CULTURE RESULTS | FAM Ct | MR | CY5 Ct | MR | AM | Comparator |
|---|---|---|---|---|---|---|---|---|
| 39 | SPUTUM | TB | 15.91 | 0.218 | 34.50 | 0.166 | Detected | high |
| 38 | SPUTUM | TB | 16.76 | 0.225 | 34.55 | 0.176 | Detected | high |
| 35 | SPUTUM | TB | 19.88 | 0.238 | 33.34 | 0.175 | Detected | high |
| 23 | SPUTUM | TB | 20.77 | 0.233 | 33.21 | 0.169 | Detected | med |
| 30 | BAL | TB | 21.79 | 0.226 | 33.18 | 0.177 | Detected | high |
| 25 | SPUTUM | TB | 22.28 | 0.222 | 33.54 | 0.171 | Detected | error |
| 61 | SPUTUM | TB | 22.84 | 0.227 | 33.96 | 0.179 | Detected | med |
| 45 | SPUTUM | TB | 23.67 | 0.227 | 33.13 | 0.177 | Detected | high |
| 44 | ASPIRATE | TB | 25.06 | 0.243 | 33.25 | 0.181 | Detected | high |
| 34 | SPUTUM | TB | 25.50 | 0.230 | 33.08 | 0.184 | Detected | med |
| 63 | SPUTUM | TB | 27.55 | 0.245 | 32.99 | 0.141 | Detected | low |
| 21 | SPUTUM | TB | 27.61 | 0.229 | 33.54 | 0.187 | Detected | med |
| 33 | ASPIRATE | TB | 27.63 | 0.247 | 33.31 | 0.182 | Detected | med |
| 26 | BAL | TB | 28.05 | 0.248 | 33.70 | 0.187 | Detected | med |
| 58 | SPUTUM | TB | 28.26 | 0.215 | 33.88 | 0.177 | Detected | med |
| 32 | SPUTUM | TB | 29.26 | 0.225 | 36.49 | 0.177 | Detected | low |
| 28 | SPUTUM | TB | 29.43 | 0.241 | 33.15 | 0.197 | Detected | low |
| 42 | SPUTUM | TB | 29.82 | 0.228 | 35.19 | 0.184 | Detected | med |
| 60 | SPUTUM | TB | 30.14 | 0.222 | 34.24 | 0.179 | Detected | low |
| 59 | SPUTUM | TB | 30.21 | 0.229 | 34.70 | 0.185 | Detected | low |
| 29 | SPUTUM | TB | 30.68 | 0.229 | 34.19 | 0.188 | Detected | low |
| 57 | SPUTUM | TB | 31.31 | 0.231 | 34.40 | 0.192 | Detected | low |
| 24 | SPUTUM | TB | 31.70 | 0.239 | 35.37 | 0.191 | Detected | low |
| 31 | SPUTUM | TB | 32.73 | 0.189 | −1 | 0.008 | Detected | low |
| 62 | SPUTUM | TB | 33.12 | 0.237 | 34.52 | 0.185 | Detected | low |
| 27 | BRONCHIA WASH | TB | 35.00 | 0.232 | 34.55 | 0.185 | Detected | Not det |
| 55 | LUNG TISSUE | TB | 36.67 | 0.212 | 34.76 | 0.176 | Detected | not tested* |
| 53 | LUNG TISSUE | TB | 37.71 | 0.277 | 35.94 | 0.177 | Detected | Not det |
| 51 | SPUTUM | TB | 38.19 | 0.142 | −1 | 0.003 | Detected | not tested* |
| 46 | SPUTUM | TB | 38.58 | 0.161 | 34.58 | 0.185 | Detected | Not det |
| 22 | BAL | TB | −1 | 0.003 | 34.05 | 0.174 | Not det | Not det |
| 36 | SPUTUM | TB | −1 | 0.006 | 34.60 | 0.191 | Not det | Not det |
| 37 | SPUTUM | TB | −1 | 0.004 | 35.90 | 0.178 | Not det | Not det |
| 40 | SPUTUM | TB | −1 | 0.004 | 34.42 | 0.178 | Not det | Not det |
| 41 | SPUTUM | TB | −1 | 0.002 | 34.79 | 0.182 | Not det | Not det |
| 43 | SPUTUM | TB | −1 | 0.004 | 34.97 | 0.165 | Not det | Not det |
| 48 | BAL | TB | −1 | 0.005 | 34.97 | 0.165 | Not det | Not det |
| 49 | SPUTUM | TB | −1 | 0.001 | 34.58 | 0.168 | Not det | Not det |
| 50 | SPUTUM | TB | −1 | 0.005 | 35.14 | 0.184 | Not det | Not det |
| 54 | SPUTUM | TB | −1 | 0.006 | 34.64 | 0.173 | Not det | Not det |

*"not tested" sample was because of not enough volume

The RealTime MTB showed better sensitivity at low end samples comparing to the comparator's assay.

Example 10

Analytical and Clinical Performance of MTB Assay

This Example describes the analytical performance of the real time MTB detection assay.

Materials and Methods

The work flow for the real time MTB assay is described in FIG. 1.

Sample Inactivation 500 mL of Inactivation reagent (IR) was prepared by combining the following components: 20 mL 10 M NaOH, 300 mL isopropanol, 0.9 mL Tween-20, and 179.1 mL purified water. Once prepared the IR was stable for up to one month at room temperature. If frozen, specimens (unprocessed specimens or processed NALCsediments) were thawed at 15° to 30° C. Approximately three volumes of IR were added to each volume of sample (the minimum allowable specimen volume is 0.3 mL). The same volume ratio of sample:IR was maintained notwithstanding the type of sample (unprocessed or NALC sediment). The mixture was vortexed twice for 20 to 30 seconds each during the first hour of room temperature incubation. The validated incubation time was one to 24 hours. The inactivation process occurred under a biohood. Once completed, the inactivated samples were removed from under a biohood and then subjected to sample preparation outside of the biohood. The inactivation process was demonstrated to effectively reduce MTB viability at three different laboratories using cultured MTB added to NALC sediments of sputum, MTB positive clinical NALC sediments, and MTB smear/culture positive sputum samples (Qi C., et al., Effectiveness of the sample inactivation procedure employed by the new Abbott Real-Time assay for the detection of *Mycobacterium tuberculosis*, 24th European Congress of Clinical Microbiology and Infectious Diseases (ECCMID) 2014).

Sample Preparation

IR-treated specimens and the assay controls were loaded onto an m2000sp instrument where DNA was isolated using guanidinium thiocyanate-magnetic microparticle technology to capture nucleic acids followed by washes to remove unbound components. An Internal Control (IC) was added at the start of sample preparation. The bound nucleic acids were eluted and transferred to a 96 deep-well plate. At the completion of sample preparation, the m2000sp was used to create an amplification master mix consisting of AmpliTaq Gold Polymerase, a magnesium chloride activation reagent, and oligonucleotide reagent containing primers, probes and dNTPs. The m2000sp was used to dispense 25 µl aliquots of the master mix followed by 25 µl aliquots of the extracted eluates to a 96-well optical reaction plate. The plate was sealed manually and transferred to the m2000rt for realtime PCR. As an alternative to the m2000sp, sample preparation, mastermix preparation, and PCR plate set-up can be performed manually.

Amplification and Detection

The m2000rt instrument was used for amplification and realtime fluorescence detection.

The detection of MTB complex members (Warren R M, et al., Int J Tuberc Lung Dis 2006; 10:818-822) was achieved through the use of two sets of primers; one targeting the insertion element IS6110 (Thierry D, et al., Nucleic Acids Res 1990; 18:188) and one the PAB gene (Anderson A B, Hansen E B Infect Immun 1989; 57:2481-2488). Signal for MTB complex detection was generated with the use of fluorescent labelled probes. The MTB dual target probes are each labeled with the fluorophore FAM at the 5' end and the Black Hole Quencher (BHQ1) at the 3' end. Thus, MTB signals from both IS6110 and PAB are detected in the same FAM channel. The amplification cycle at which FAM fluorescent signal is detected is proportional to the log of the MTB DNA concentration present in the original sample. The probe for internal control (IC) is labelled with Quasar at the 5' and Black Hole Quencher BHQ2 at the 3' end to allow IC and target signals to be distinguishable in a single PCR well.

Assay Controls

A minimum of one replicate of the Negative Control and one replicate of the Positive Control were used to determine run validity. The Negative Control consisted of TE buffer and preservatives. The Positive Control consisted of plasmid DNA containing both the IS6110 and PAB target sequences diluted in TE buffer with 1.5 g/mL of poly dA:dT and preservatives. The IC consisted of plasmid DNA containing a pumpkin hydroxypyruvate reductase (HPR) insert diluted in TE buffer with 1.5 g/mL of poly dA:dT and preservatives. IC was added at the start of sample preparation, serving as a control for sample preparation recovery, sample inhibition, and amplification efficiency. The IC did not control for the inactivation procedure. The IC threshold cycle (Ct) value difference between each sample and the run controls was used to assess the validity of each sample result.

Panels and Clinical Specimens

MTB Complex Subspecies:

Nineteen MTB complex subspecies DNA samples were obtained from the American Type Culture Collection (ATCC, Manassas, Va.) and one (*M. canettii*) was provided kindly by Ibis Biosciences (Carlsbad, Calif.). A total of 20 MTB complex strains was tested including *M. africanum* 25420, *M. africanum* 35711, *M. bovis* 35735, *M. bovis* 19274, *M. bovis* BCG 35746, *M. bovis* BCG 35747D, *M. canettii*, *M. caprae* BAA-824D, *M. microti* 11152, *M. microti* 19422, *M. pinnipedii* BAA-688D, MTB 25177D-5 (H37Ra), MTB 25618D-5 (H37Rv), MTB BAA-2236D, MTB BAA-2237D, MTB 27294D, MTB BAA-2234D, MTB 35822D, MTB 35838D, MTB BAA-2235D. Additionally, 46 strains of the MTB subspecies including the three principal genetic groups and nine genetic clusters were obtained from Dr. Barry Kreiswirth at the University of Medicine and Dentistry New Jersey (Newark, N.J.) (Mathema B, et al., Current Insights, Clinical Microbiology Reviews 2006; 19:658-685). The DNA of the 20 MTB complex subspecies obtained from ATCC and Ibis were directly tested using reported DNA concentrations as determined by the PicoGreen® NanoDrop method. The other 46 DNA concentrations were determined using PicoGreen® NanoDrop measurements at Abbott Molecular with the exception of three samples where such measurements could not be obtained due to low volume and impurities. These three samples were diluted at a sample to water ratio of 1:600 and tested directly.

Limit of Detection [LOD]:

An MTB H37Rv panel targeted to $1 \times 10^5$ colony forming units (cfu)/mL was prepared by Zeptometrix (Buffalo, N.Y.). Three one mL aliquots of the Zeptometrix panel were combined and centrifuged at 3,000×g for 15 minutes to remove free MTB DNA in the supernatant. The cell pellet was resuspended in three mL of TE buffer to maintain the concentration of $1 \times 10^5$ cfu/mL. The cells were then added to a pool of sputum, which was homogenized using bead-beating, to make the following MTB-containing dilution panels: 80 cfu/mL, 50 cfu/mL, 25 cfu/mL, 10 cfu/mL, 5 cfu/mL, 1 cfu/mL, 0.50 cfu/mL, 0.10 cfu/mL, and 0.05 cfu/mL.

Analytical Specificity:

Analytical specificity panel members were collected as follows: Cytomegalovirus, Herpes Simplex virus 1, and Varicella-zoster virus were obtained from Advanced Biotechnology Inc. (Columbia, Md.), 69 mycobacterial and other microorganism species were obtained from ATCC, and eight bacterial isolates were cultured at Abbott Molecular.

Potentially Interfering Substances:

The following materials were obtained for this testing: blood, DNA from human cells, gastric acid, hypertonic saline, physiologic saline, culture media, NALC pellet material, five anti-TB medications (Isoniazid, Rifampicin, Streptomycin, Pyrazinamide, Ethambutol), and bovine mucus.

Carryover:

Two samples were prepared: a high positive MTB sample containing $1 \times 10^7$ copies/mL of a plasmid containing the assay target sequences and a negative sample.

Reproducibility:

Two samples were prepared: a positive sample containing an MTB concentration of ~three times the claimed assay LOD and a negative sample.

Clinical Specimens:

198 sputum specimens were collected by Discovery Life Sciences (Los Osos, Calif.) from TB suspect patients in Russia, South Africa, Uganda, and Vietnam. 150 sputum specimens from Vietnam were obtained from the specimen bank operated by the Foundation for Innovative New Diagnostics (FIND) (Geneva, Switzerland). 234 NALC specimens were obtained from Northwestern University Memorial Hospital (Chicago, Ill.). All patient specimens were collected under ethical guidelines. The HIV status of the patients was not determined. For all specimens smear (when available) and culture testing was performed near the collection site, while Abbott RealTime MTB assay testing was performed at Abbott Molecular.

Results

MTB Complex Subspecies Detection

This study was conducted to determine whether the specific primers and probes used in MTB assays would detect the following eight MTB complex sub-species: *M.*

Figure 2:
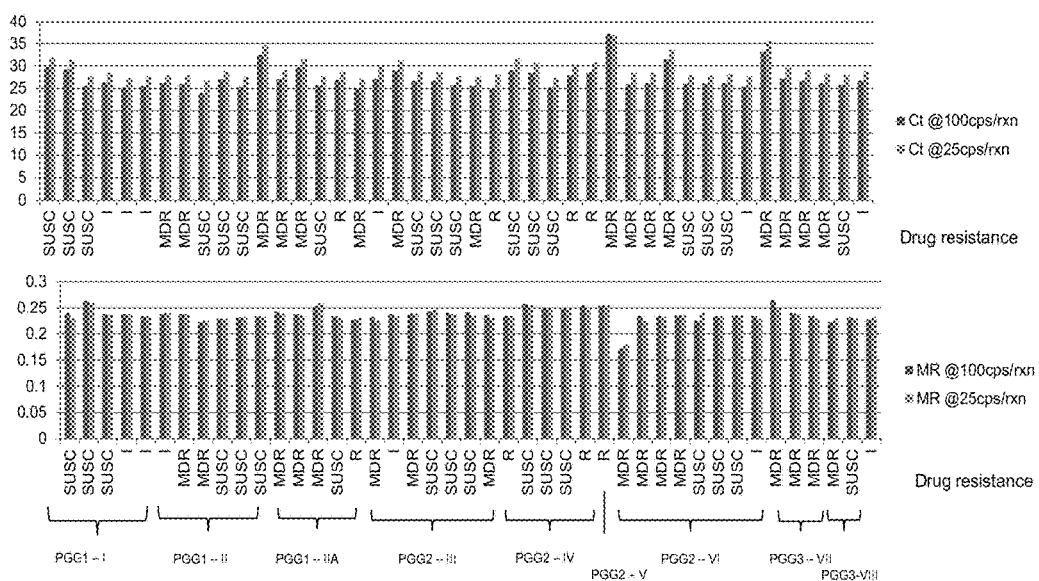
FIG. 2 shows data from detection of 46 MTB phylogenetically and geographically diverse MTB isolates.
Figure 3:
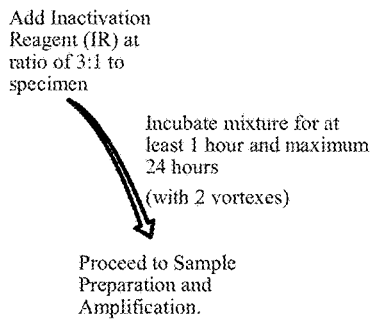
FIG. 3 shows an MTB assay work-flow diagram for sample preparation.
Figure 4:
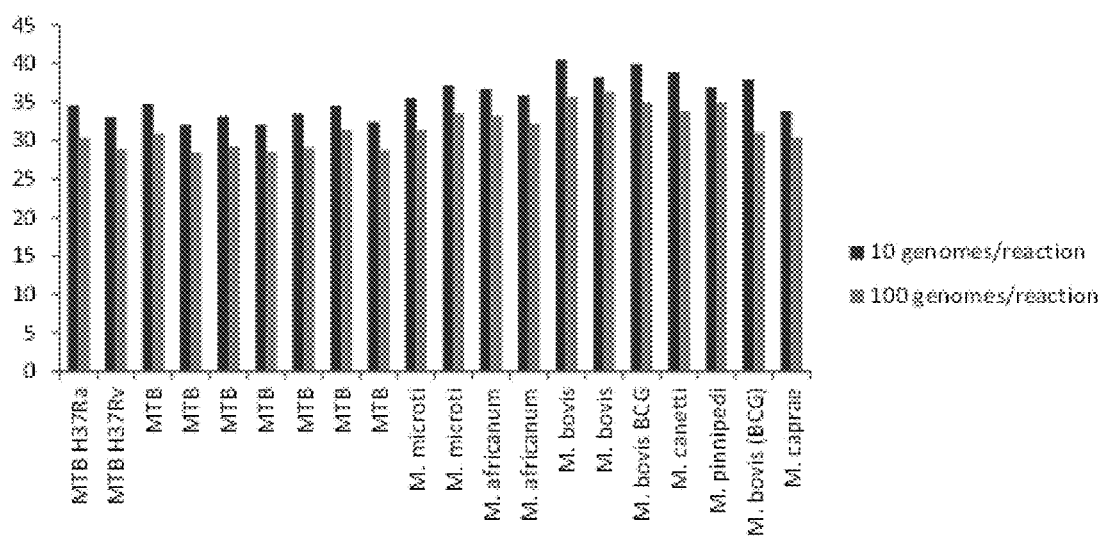
FIG. 4 shows mean cycle number values determined when MTB complex genomic DNAs were tested to determine assay inclusivity.

*africanum, M. bovis, M. bovis* BCG, *M. canettii, M. caprae, M. microti, M. pinnipedii,* and *M. tuberculosis.* Two sets of purified MTB complex DNAs were tested. The first set of 20 purified DNAs contained representatives of the previously mentioned MTB sub-species. Each purified DNA was tested at two concentrations (100 and 10 genomes/reaction) with four replicates being tested per concentration. At the 100 MTB genomes per reaction level, all four replicates of each of the 20 MTB strains were detected. At the 10 MTB genomes per reaction level, all four replicates of 17 of the strains were detected. For three strains (two *M. bovis* and one *M. bovis* BCG) two of the four replicates were detected (FIG. 4). The second set of 46 MTB strains from the MTB sub-species were tested at two concentrations: 100 genomes/reaction and 25 genomes/reaction. Four replicates of each DNA were tested at each concentration. All the tested replicates were positive at both concentrations (FIG. 2).

Limit of Detection (LOD)

A nine-level dilution series was made from MTB strain H37Rv cells diluted in a glass bead homogenized sputum pool. The panel members in the dilution series were targeted to the following concentrations: 80 cfu/mL, 50 cfu/mL, 25 cfu/mL, 10 cfu/mL, 5 cfu/mL, 1 cfu/mL, 0.50 cfu/mL, 0.10 cfu/mL, and 0.05 cfu/mL. Twenty replicates of each panel member were tested across four runs using the Abbott RealTime MTB assay. The study was conducted using one lot of MTB assay and control reagents. The significance level for this study was 0.05. The detection rate was calculated for each target concentration (Table 11). A Probit regression model was fitted, based on the target concentrations and the detection rate using PROC PROBIT in SAS, with the target concentration (X) as the independent variable and the detection rate P (Y=1) as the response variable. The Probit analysis of the data determined that the concentration of MTB detected with 95% probability was 2.45 cfu/mL (95% CI 1.44-6.10 cfu/mL). The claimed analytical sensitivity of the Abbott RealTime MTB assay is 17 cfu/mL in pooled homogenized sputum using the MTB H37Rv strain.

Analytical Specificity

Each of the 80 potential cross-reactants was tested in both an MTB positive sample and an MTB negative sample. Nucleic acid from each potentially cross-reacting mycobacterium, virus, or other microorganism at a targeted concentration of $1\times10^5$ to $1\times10^7$ copies or genomes per mL was added to the MTB positive samples (containing 1,000 MTB genomes/mL) and the MTB negative samples. Cultured microorganisms at a target concentration of $1\times10^6$ cfu/mL were added to the MTB positive samples and the MTB negative samples. The assay results for all 80 negative samples were reported as "MTB Not Detected". The assay results for all 80 MTB-containing samples were reported as "MTB Detected" (Table 7).

Potentially Interfering Substances

The potential for interference in the test results was assessed with substances that may be present in the respiratory system. MTB negative and MTB positive (500 copies/mL) samples were tested in the absence or the presence of each potentially interfering substance with elevated levels of bovine mucus, blood, DNA from human cells, gastric acid, hypertonic saline, physiological saline, culture media, NALC pellet material and five anti-TB medications (Isoniazid, Rifampicin, Streptomycin, Pyrazinamide, Ethambutol) (Table 12). The results showed no interference in the performance of the MTB assay in the presence of high levels of blood, DNA from human cells, gastric acid, hypertonic saline, physiological saline, culture media, NALC pellet material and five anti-TB medications (Isoniazid, Rifampicin, Streptomycin, Pyrazinamide, Ethambutol). Interference of the Abbott RealTime MTB assay was observed in the presence of bovine mucus at 8.3% (all five replicates were false negative or inhibited) and 5.0% (one of five replicates was false negative). No interference was found at bovine mucus concentrations of 2.5% or less.

Carryover

To evaluate the potential of carryover from high positive MTB samples to negative samples when using the Abbott RealTime MTB assay, five m2000 system runs each consisting of 96 samples (Positive Control, Negative Control, 46 high positive samples at $1\times10^7$ copies/mL and 46 negative samples) in which the high positive samples were interspersed among negative samples. The MTB concentration in the high positive sample of $1\times10^7$ copies/mL resulted in a Ct value that was earlier than 95% or more of the results obtained from specimens of the MTB positive population tested with the MTB assay. The assay did not exhibit any carryover from high positive samples to the 230 negative samples in the five runs. A 96 sample run was completed in less than 8 hours.

Reproducibility

A reproducibility test was performed to evaluate the Abbott RealTime MTB assay repeatability in the m2000 system and the compatibility between the Abbott m2000sp instrument and the manual sample preparation method. The study was performed with a positive panel at three times the claimed LOD level and a negative panel. The study was conducted by four operators using two lots of MTB amplification reagents: two operators performing runs using an Abbott m2000sp instrument and two operators performing runs using manual sample preparation. For each sample preparation method, the two operators each used one unique lot of Abbott RealTime MTB amplification reagents and tested each panel member in replicates of eight, once per day, for five days, for a total of 40 replicates per panel member (80 total replicates per panel member per method; 160 total tested with m2000sp instrument sample preparation and 160 total tested with manual sample preparation). The overall agreement with expected results was 100% (159/159, one sample was invalid because of an instrument error) with a lower 95% CI of 98.1% for samples prepared with the Abbott m2000sp instrument or with manual sample preparation. The MTB assay is compatible with both the Abbott m2000sp instrument and the Abbott manual sample preparation method.

Clinical Sensitivity and Specificity

One sputum or one NALC sediment was tested from each of 582 TB suspect patients. Samples were collected from Russia, South Africa, Uganda, the United States, and Vietnam. Each specimen was split to allow testing of MTB on one aliquot and smear and culture on the second aliquot. The testing samples were blinded and final result decoding was performed by AM statistical group. For MTB testing, two specimens generated an invalid IC result, and an additional four specimen results gave m2000 error codes. The frequency of clinical specimens with invalid results measured by inhibition was 0.3% (2/582), while the invalid rate including both inhibition and instrument errors was 1.0% (6/582). Five culture negative specimens that were positive by both the MTB assay described herein and a commercially available MTB NAAT were excluded from the analysis. A total of 571 valid samples were included for data analysis. The overall MTB sensitivity versus culture was 93% (198/212). The assay sensitivity was 99% (147/149) in smear positive, culture positive specimens, and 81% (51/63) in smear negative, culture positive samples. The specificity was 97% (348/359) (Table 13). 76 of the MTB negative samples contained Non-Tuberculous Mycobacteria (NTM). Of these, 38 were MAC (*M. avium* complex), seven were *M. gordonae*, five were *M. kansasii*, five were *M. chelonae/abcessus*, three were *M. xenopi*, and 18 contained other mycobacterial species. With the MTB assay described herein, all of the NTM sample results were "MTB Not Detected" with the exception of two samples that produced "MTB Detected" results with late CN (>38) values as compared to the assay cutoff of 40. The specificity value of 97% resulted from testing the NTM population is similar to the specificity observed when testing the non-NTM population. Furthermore 500 non-TB suspect patient sputum samples collected from within the U.S. population showed 100% TB negative test results.

TABLE 11

Limit of Detection

| Target Concentration (cfu/mL) | Number Tested | Number Detected | Detection Rate | Percent Detected |
|---|---|---|---|---|
| 80 | 20 | 20 | 1.00 | 100 |
| 50 | 20 | 20 | 1.00 | 100 |
| 25 | 20 | 20 | 1.00 | 100 |
| 10 | 20 | 20 | 1.00 | 100 |
| 5 | 20 | 20 | 1.00 | 100 |
| 1 | 20 | 18 | 0.90 | 90 |
| 0.50 | 20 | 7 | 0.35 | 35 |
| 0.10 | 20 | 2 | 0.10 | 10 |
| 0.05 | 20 | 1 | 0.05 | 5 |

A probit analysis of the Abbott RealTime MTB data determined that the concentration of MTB detected with 95% probability was 2.45 cfu/mL at CN cutoff 40 (95% Confidence Interval of 1.44-6.10 cfu/mL).

TABLE 12

Potential interfering substances and their concentrations/percentages tested to determine susceptibility to interfering substances

| Potentially Interfering Substance | Specimen Source | Concentration/Percentage |
|---|---|---|
| Mucus | Sputum | Mucin 5% (w/v) |
| Blood | Sputum or BAL | 5% (v/v) |
| DNA from human cells | Sputum, BAL, NALC Sediments of Sputum/BAL | $10^6$ cells/mL |
| Gastric acid | Sputum/BAL | pH 3 to 4 HCl in water, neutralized to pH 6 to 8 with sodium bicarbonate |
| Hypertonic saline used to induce sputum | Sputum | NaCl (5% w/v) |
| Physiologic saline used to collect BAL | BAL | NaCl (0.9% w/v) |
| Culture media | MTB culture | 100% |
| Material used to resuspend NALC pellets | NALC pellets | 0.067M phosphate, pH 6.8 |
| Isoniazid (Anti-TB medication) | Sputum or BAL | 90 mg/mL |
| Rifampicin/Rifampin (Anti-TB medication) | Sputum or BAL | 120 ug/mL |
| Streptomycin (Anti-TB medication) | Sputum or BAL | 400 ug/mL |
| Pyrazinamide (Anti-TB medication) | Sputum or BAL | 500 ug/mL |
| Ethambutol (Anti-TB medication) | Sputum or BAL | 60 ug/mL |

TABLE 13

Sensitivity and specificity obtained when testing clinical specimens

| | Culture/Smear results | | | |
|---|---|---|---|---|
| | Sensitivity | | | Specificity |
| | C+/S+ | C+/S− | C+ | C− |
| RealTime MTB | 99% (147/149) | 81% (51/63) | 93% (198/212) | 97% (348/359) |

Example 11

Inactivation Reagents

This example describes inactivation reagents for use in MTB detection assays. The assay is a NAAT for the detection of MTB complex DNA in respiratory specimens (sputum, bronchial alveolar lavage (BAL) and N-acetyl-L-cysteine (NALC) sediments of sputum and bronchial alveolar lavarge (BAL). A sample inactivation reagent and procedure were developed to liquefy viscous samples and to reduce MTB viability to allow for safe testing of samples outside biosafety cabinets. The study was to assess the effectiveness of the sample inactivation procedure and to determine the stability of the Inactivation Reagent (IR).

For the viscosity reduction study, 150 sputum samples were mixed with IR (0.6% sodium hydroxide [w/v], 60% isopropanol [v/v], and 1.8% Tween-20 [v/v]) at a ratio of 1:2 or 1:3. The mixtures were vortexed vigorously and incubated at room temperature. The mixture was vortexed again after 20 to 30 minutes of incubation. Reduction of viscosity was assessed by visual examined after 30 minutes, 60 minutes, and 24 hours of incubation.

For the inactivation study, two MTB clinical isolates and MTB ATCC 27294 isolate were used to prepare mock MTB positive respiratory samples by mixing one mL of MTB cell suspension in the concentrations of $1\times10^6$, $1\times10^7$, or $1\times10^8$ cfu/mL with four mL of pooled MTB negative NALC treated respiratory sample. Each mock MTB NALC sample was then mixed with IR at ratios of 1:2 or 1:3. A mock sample treated with sterile PBS buffer at a sample to PBS ratio of 1:2 was used as the positive control. Negative controls were prepared by adding sterile PBS to the pooled MTB negative NALC sample at a ratio of PBS to NALC of 1:2. All samples/controls were vortexed vigorously and incubated for 60 minutes at room temperature. Vortexing was repeated 30 minutes into the incubation. At the end of the incubation, the IR treated samples were transferred into new 50 mL tubes, vortexed and centrifuged for 15 minutes at 3000×g. The sediment was re-suspended in 10 mL sterile PBS and centrifuged for an additional 15 minutes at 3000×g. Pellets were each re-suspended in 10 mL sterile PBS. One mL of the suspension was used to inoculate a Mycobacterial Growth Indicator Tube (MGIT). The final MTB added to each MGIT culture ranged from 1-2×10$^4$ to 1-2×10$^6$ cfu. In addition, a total of 51 MTB positive clinical NALC sediments of sputum, 20 from Northwestern Memorial hospital and 31 from Lancet Laboratories, were tested for growth after the IR treatment at a sample to IR ratio of 1:3 with the same procedure. Ten of the 20 samples from Northwestern Memorial Hospital were treated at a sample to IR ratio of 1:2. The remaining 41 samples were treated with a sample to IR ration of 1:3. Culture was performed with BACTEC MGIT 960 system (Becton Dickinson, Sparks, Md.) for 42 days. Positive growth was identified with Gen-Probe Accuprobe® system (Gen-Probe Inc, San Diego, Calif.). Initial studies to demonstrate the inactivation efficiency of direct respiratory samples (MTB smear and culture positive sputum samples) were also performed in combination with an IR stability study as described in the following paragraph.

To determine the optimal storage condition for IR, three aliquots of IR were stored for 39 days at storage conditions of 15-30° C. and 33-37° C. in glass or polypropylene bottles. Each aliquot of IR at each storage condition was examined for changes in appearance and volume and tested for MTB inactivation efficacy after 39 days of storage with 12 MTB smear and culture positive sputum samples obtained from SAGE Bio Networks (Dhaka, Bangladesh) and Foundation for Innovative New Diagnostics (FIND) MTB specimen bank using a 1:3 sample to IR ratio. An MTB strain H37Rv cell panel obtained from Zeptometrix Corporation (Buffalo, N.Y.) was used as the Positive Control.

The viscosity reduction study showed that 60 minutes of incubation was sufficient to reduce the viscosity of the samples. For the inactivation study, none of the mock MTB samples prepared with the three MTB isolates at $1\times10^8$, $1\times10^7$, and $1\times10^6$ cfu/mL showed MTB growth after being treated with IR at a sample to IR ratio of 1:3. One IR-treated sample, prepared with $1\times10^7$ cfu/mL MTB and treated with IR at a sample to IR ratio of 1:2, showed growth after 27 days of incubation, although two repeats at the same bacterial concentration tested negative for growth. None of the 20 MTB positive NALC sputum sediments showed MTB growth following the treatment with IR at a sample to IR ratio of 1:2 or 1:3. Further, 31 clinical NALC sputum sediments that had previously tested positive for MTB by culture were tested negative for MTB growth after receiving IR treatment at 1:3 sample to IR ratio.

Changes in appearance after storage were not observed after 39 days. A volume loss of 0 to 6% was observed after 39 days of storage. The highest volume loss of 6% was observed when IR was stored in polypropylene containers at 33-37° C. However, the efficiency of the IR solution to inactivate MTB was not affected after storage. The 12 MTB positive sputum samples showed no growth after being treated with the IR stored under the various conditions described above.

It was noted that some MTB in clinical samples survived the recommended Cepheid GeneXpert MTB/RIF sample inactivation process (15 minute incubation period and a 1:2 sample to Sample Reagent ratio) (Banada, P. P., et al., 2010. J. Clin. Microbiol. 48:3551-3557). The authors suggested complete MTB inactivation may require a longer incubation time. Experimental data generated by the study described herein demonstrated that sample inactivation performed for 60 minutes using the recommended vortexing steps was sufficient for complete MTB inactivation.

When a 1:2 sample to IR ratio was used, one replicate of a $1\times10^7$ MTB cfu/mL culture ($2\times10^5$ cfu/mL in the MGIT culture) showed growth after 27 days of incubation of the MGIT culture. A previous study showed that MGIT cultures containing 10 cfu/mL of MTB became positive after 16 days of incubation, the result suggested that a very low number MTB survived the inactivation process when a 1:2 sample to IR ratio was used (Tortoli, E., P. et al., J. Clin. Microbiol. 37(11):3578-3582; Wallis, et al., 1999. Antimicrobial Agents and Chemotherapy, 43:2600-2606). To achieve the optimal inactivation efficiency, the sample to IR ratio of 1:3 was used for the rest of the inactivation experiments.

In conclusion, the IR evaluated in this study was able to liquefy sputum samples and to achieve effective inactivation of MTB in clinical specimens when treated with IR at a sample to IR ratio of 1:3 for 60 minutes. This inactivation procedure enables these samples to be safely handled outside of a biosafety cabinet after the proper inactivation procedure.

---

We claim:

1. A method of identifying *Mycobacterium tuberculosis* (MTB) nucleic acid in a biological sample, comprising:
   a) contacting a biological sample from a subject with at least two nucleic acid primer pairs selected from the group consisting of SEQ ID NOS: 1-4, 7 and 8 and at least two probes selected from the group consisting of SEQ ID NOS: 5, 6 and 9, and b) detecting the binding of said nucleic acid primer or probe to said MTB nucleic acid.

2. The method of claim 1, wherein said detecting comprises real time PCR.

3. The method of claim 1, wherein said method further comprises the step of inactivating said MTB in said sample using an inactivation reagent prior to said contacting.

4. The method of claim 3, wherein said inactivation reagent comprises water, a detergent, an alcohol, and NaOH.

5. The method of claim 3, wherein said inactivation reagent comprise isopropanol, sodium hydroxide, polyoxyethylene (2) sorbitan monolaurate, and water.

6. The method of claim 1, wherein said sample is sputum, bronchoalveolar lavage [BAL], or N-acetyl-L-cysteine [NALC] sediments of sputum.

7. The method of claim 1, wherein one or more of said SEQ ID NOS comprises a label.

8. The method claim 7, wherein said label comprises a fluorophore.

9. The method of claim 8, wherein said label comprises a fluorophore/quencher pair.

10. The method of claim 1, further comprising contacting said biological sample from said subject with one or more nucleic acid sequences selected from the group consisting of SEQ ID NOS: 10-36.

11. The method of claim 1, further comprising contacting said biological sample from said subject with a reaction mixture.

12. The method of claim 11, wherein said reaction mixture comprises a reagent selected from a nucleic acid polymerase, a plurality of dNTPs, a buffer and an inactivation agent.

13. The method of claim 1, further comprising contacting said biological sample from said subject with guanidinium thiocyanate and a magnetic microparticle.

* * * * *

UNITED STATES PATENT AND TRADEMARK OFFICE
CERTIFICATE OF CORRECTION

PATENT NO. : 10,072,306 B2
APPLICATION NO. : 14/793241
DATED : September 11, 2018
INVENTOR(S) : Ning Tang et al.

Page 1 of 1

It is certified that error appears in the above-identified patent and that said Letters Patent is hereby corrected as shown below:

In the Claims

Claim 5, Column 51, Lines 29-31 read:
"The method of claim 3, wherein said inactivation reagent comprise isopropanol, sodium hydroxide, polyoxyethylene (2) sorbitan monolaurate, and water."
Whereas it should read:
"The method of claim 3, wherein said inactivation reagent comprises isopropanol, sodium hydroxide, polyoxyethylene 20 sorbitan monolaurate, and water."

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 36

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
cctgcgagcg taggcgtcgg tga                                              23

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
cgtccagcgc cgcttcggac ca                                               22

<210> SEQ ID NO 3
<211> LENGTH: 27
<212> TYPE: DNA
<213> ORGANISM: Artificial Sequence
<220> FEATURE:
<223> OTHER INFORMATION: Synthetic
```

```
<400> SEQUENCE: 3
gcacctcaag ctgaacggaa aagtcct                                              27

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
ccggggttga gcgcagcgat ct                                                   22

<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' propynyl Du
<220> FEATURE:
<221> NAME/KEY: misc_feature
<222> LOCATION: (5)..(5)
<223> OTHER INFORMATION: 5' propynyl Du
<220> FEATURE:
<221> NAME/KEY: misc_feature
<222> LOCATION: (10)..(10)
<223> OTHER INFORMATION: 5' propynyl Du
<220> FEATURE:
<221> NAME/KEY: misc_feature
<222> LOCATION: (11)..(11)
<223> OTHER INFORMATION: 5' propynyl dC
<220> FEATURE:
<221> NAME/KEY: misc_feature
<222> LOCATION: (12)..(12)
<223> OTHER INFORMATION: 5' propynyl Du
<220> FEATURE:
<221> NAME/KEY: misc_feature
<222> LOCATION: (14)..(14)
<223> OTHER INFORMATION: 5' propynyl dC
<220> FEATURE:
<221> NAME/KEY: misc_feature
<222> LOCATION: (15)..(15)
<223> OTHER INFORMATION: 5' propynyl Du
<220> FEATURE:
<221> NAME/KEY: misc_feature
<222> LOCATION: (17)..(19)
<223> OTHER INFORMATION: 5' propynyl dC

<400> SEQUENCE: 5
naggngaggn nngnnannnt                                                      20

<210> SEQ ID NO 6
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' propynyl Du
<220> FEATURE:
<221> NAME/KEY: misc_feature
<222> LOCATION: (3)..(4)
<223> OTHER INFORMATION: 5' propynyl dC
<220> FEATURE:
<221> NAME/KEY: misc_feature
<222> LOCATION: (9)..(9)
```

```
<223> OTHER INFORMATION: 5' propynyl dC
<220> FEATURE:
<221> NAME/KEY: misc_feature
<222> LOCATION: (11)..(12)
<223> OTHER INFORMATION: 5' propynyl dC
<220> FEATURE:
<221> NAME/KEY: misc_feature
<222> LOCATION: (14)..(14)
<223> OTHER INFORMATION: 5' propynyl Du
<220> FEATURE:
<221> NAME/KEY: misc_feature
<222> LOCATION: (15)..(15)
<223> OTHER INFORMATION: 5' propynyl dC

<400> SEQUENCE: 6
nannagggna nnannaaat                                             19

<210> SEQ ID NO 7
<211> LENGTH: 28
<212> TYPE: DNA
<213> ORGANISM: Artificial Sequence
<220> FEATURE:
<223> OTHER INFORMATION: Synthetic

<400> SEQUENCE: 7
ctacagcaga gttggcagct tcactttc                                   28

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
gtctggcctt tcagcaagtt tc                                         22

<210> SEQ ID NO 9
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 5' propynyl dC
<220> FEATURE:
<221> NAME/KEY: misc_feature
<222> LOCATION: (7)..(8)
<223> OTHER INFORMATION: 5' propynyl Du
<220> FEATURE:
<221> NAME/KEY: misc_feature
<222> LOCATION: (9)..(9)
<223> OTHER INFORMATION: 5' propynyl dC
<220> FEATURE:
<221> NAME/KEY: misc_feature
<222> LOCATION: (11)..(11)
<223> OTHER INFORMATION: 5' propynyl Du
<220> FEATURE:
<221> NAME/KEY: misc_feature
<222> LOCATION: (17)..(17)
<223> OTHER INFORMATION: 5' propynyl dC

<400> SEQUENCE: 9
gangagnnna ngagggnat                                             19

<210> SEQ ID NO 10
<211> LENGTH: 26
<212> TYPE: DNA
<213> ORGANISM: Artificial Sequence
```

```
<220> FEATURE:
<223> OTHER INFORMATION: Synthetic

<400> SEQUENCE: 10
gccgcttcgg accaccagca cctaac                                              26

<210> SEQ ID NO 11
<211> LENGTH: 28
<212> TYPE: DNA
<213> ORGANISM: Artificial Sequence
<220> FEATURE:
<223> OTHER INFORMATION: Synthetic

<400> SEQUENCE: 11
gtaggcgtcg gtgacaaagg ccacgtag                                            28

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
tgcccaggtc gacacata                                                       18

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
tacgaccaca tcaaccggga gccca                                               25

<210> SEQ ID NO 14
<211> LENGTH: 25
<212> TYPE: DNA
<213> ORGANISM: Artificial Sequence
<220> FEATURE:
<223> OTHER INFORMATION: Synthetic

<400> SEQUENCE: 14
gcgtggacgc ggctgatgtg ctcct                                               25

<210> SEQ ID NO 15
<211> LENGTH: 17
<212> TYPE: DNA
<213> ORGANISM: Artificial Sequence
<220> FEATURE:
<223> OTHER INFORMATION: Synthetic

<400> SEQUENCE: 15
ccgcgagctg cgcgatg                                                        17

<210> SEQ ID NO 16
<211> LENGTH: 28
<212> TYPE: DNA
<213> ORGANISM: Artificial Sequence
<220> FEATURE:
<223> OTHER INFORMATION: Synthetic

<400> SEQUENCE: 16
gcacgctgct ctaccgctg ttcaacct                                             28
```

```
<210> SEQ ID NO 17
<211> LENGTH: 26
<212> TYPE: DNA
<213> ORGANISM: Artificial Sequence
<220> FEATURE:
<223> OTHER INFORMATION: Synthetic

<400> SEQUENCE: 17
gtgccctgag cggtgatcgt gacgtt                                              26

<210> SEQ ID NO 18
<211> LENGTH: 17
<212> TYPE: DNA
<213> ORGANISM: Artificial Sequence
<220> FEATURE:
<223> OTHER INFORMATION: Synthetic

<400> SEQUENCE: 18
tccggccttt cacgaga                                                        17

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
tcggggctcg ggtagaagtt                                                     20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tcgtcaactc gggcagcaac                                                     20

<210> SEQ ID NO 21
<211> LENGTH: 17
<212> TYPE: DNA
<213> ORGANISM: Artificial Sequence
<220> FEATURE:
<223> OTHER INFORMATION: Synthetic

<400> SEQUENCE: 21
tactcggctc acgcacg                                                        17

<210> SEQ ID NO 22
<211> LENGTH: 24
<212> TYPE: DNA
<213> ORGANISM: Artificial Sequence
<220> FEATURE:
<223> OTHER INFORMATION: Synthetic

<400> SEQUENCE: 22
ggctcgggta gaagttcgac ttgg                                                24

<210> SEQ ID NO 23
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 23
gtcaactcgg gcagcaacga c                                              21

<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
ctcacgcacg gcggtattc                                                 19

<210> SEQ ID NO 25
<211> LENGTH: 17
<212> TYPE: DNA
<213> ORGANISM: Artificial Sequence
<220> FEATURE:
<223> OTHER INFORMATION: Synthetic

<400> SEQUENCE: 25
ggcagcggac tcgggtt                                                   17

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
accgcagttc gggctctc                                                  18

<210> SEQ ID NO 27
<211> LENGTH: 17
<212> TYPE: DNA
<213> ORGANISM: Artificial Sequence
<220> FEATURE:
<223> OTHER INFORMATION: Synthetic

<400> SEQUENCE: 27
tcacgacgac gagcgac                                                   17

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
cgctgatgac cagtgtgttg att                                            23

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
gcagcatcag atcgagcagg ac                                             22

<210> SEQ ID NO 30
```

```
<211> LENGTH: 17
<212> TYPE: DNA
<213> ORGANISM: Artificial Sequence
<220> FEATURE:
<223> OTHER INFORMATION: Synthetic

<400> SEQUENCE: 30
atggtccggc agctctc                                                     17

<210> SEQ ID NO 31
<211> LENGTH: 26
<212> TYPE: DNA
<213> ORGANISM: Artificial Sequence
<220> FEATURE:
<223> OTHER INFORMATION: Synthetic

<400> SEQUENCE: 31
caacatcagc ctgcccagtt actacc                                           26

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
cttcgcgtgg agtggacgat g                                                21

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
aagtcgctgg aaaattacat                                                  20

<210> SEQ ID NO 34
<211> LENGTH: 27
<212> TYPE: DNA
<213> ORGANISM: Artificial Sequence
<220> FEATURE:
<223> OTHER INFORMATION: Synthetic

<400> SEQUENCE: 34
cgtggaggcg atcacaccgc agacgtt                                          27

<210> SEQ ID NO 35
<211> LENGTH: 26
<212> TYPE: DNA
<213> ORGANISM: Artificial Sequence
<220> FEATURE:
<223> OTHER INFORMATION: Synthetic

<400> SEQUENCE: 35
cgttgatcaa catccggccg gtggtc                                           26

<210> SEQ ID NO 36
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 36
cggtctgtca cgtgagcgtg c                                               21
```